(12) United States Patent
Abrams et al.

(10) Patent No.: US 8,283,481 B2
(45) Date of Patent: Oct. 9, 2012

(54) INHIBITORS OF A 9-CIS EPOXYCAROTENOID DIOXYGENASE

(75) Inventors: Suzanne R. Abrams, Saskatoon (CA); Michele C. Loewen, Saskatoon (CA); Jason Boyd, Saskatoon (CA); Adrian John Cutler, Saskatoon (CA); Yuanzhu Gai, Saskatoon (CA); Kenneth M. Nelson, Saskatoon (CA)

(73) Assignee: National Research Council of Canada, Ottawa, ON (CA)

( * ) Notice: Subject to any disclaimer, the term of this patent is extended or adjusted under 35 U.S.C. 154(b) by 555 days.

(21) Appl. No.: 12/458,781

(22) Filed: Jul. 22, 2009

(65) Prior Publication Data

US 2010/0160166 A1 Jun. 24, 2010

Related U.S. Application Data

(60) Provisional application No. 61/193,799, filed on Dec. 23, 2008.

(30) Foreign Application Priority Data

Dec. 23, 2008 (CA) .................................. 2647900

(51) Int. Cl.
C07D 313/00 (2006.01)
C07C 49/00 (2006.01)
A01N 41/12 (2006.01)

(52) U.S. Cl. .................. 549/546; 568/376; 514/609
(58) Field of Classification Search .................. None
See application file for complete search history.

(56) References Cited

U.S. PATENT DOCUMENTS 2,993,864 A 7/1961 Monroe et al.
(Continued)

FOREIGN PATENT DOCUMENTS
WO WO 94/15467 7/1994
(Continued)

OTHER PUBLICATIONS

Abrams, S.R. et al. "Studies on ABA metabolism". Presentation at the Plant Metabolism meeting in Banff, Alberta, Jul. 30, 2008.
(Continued)

*Primary Examiner* — Karl J Puttlitz
(74) *Attorney, Agent, or Firm* — Hans Koenig

(57) ABSTRACT

A compound of formula (I):

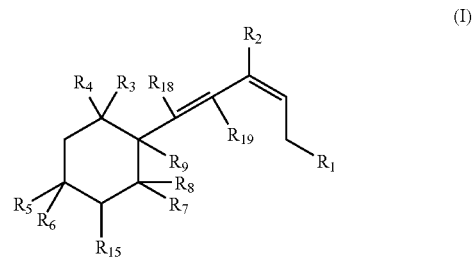

wherein:
$R_1$ is —$SR_{10}$, —O—C(O)—$R_{11}$, —$NR_{12}R_{13}$, where $R_{10}$ is a $C_{1-8}$-alkyl group or a phenyl group unsubstituted or substituted by a $C_{1-4}$-alkyl group, $R_{11}$ is a thiophenenyl, furanyl or pyrrolyl group, $R_{12}$ is H or a $C_{1-4}$-alkyl group and $R_{13}$ is a $C_{1-8}$-alkyl group or a phenyl group unsubstituted or substituted by a $C_{1-4}$-alkyl group;
$R_2$ is H or a $C_{1-4}$-alkyl group;
$R_3$ and $R_4$ are independently H or $C_{1-4}$-alkyl groups;
$R_5$ and $R_6$ are independently H, OH or $OR_{14}$, or taken together are =O, where $R_{14}$ is a protecting group;
$R_7$ is H or a $C_{1-4}$-alkyl group; and,
$R_8$ is H, $R_9$ is OH and $R_{15}$ is H, or $R_{15}$ is H and $R_8$ and $R_9$ taken together are —O—, or $R_9$ is OH and $R_8$ and $R_{15}$ taken together form a bond; and,
$R_{18}$ and $R_{19}$ are both H, or $R_{18}$ and $R_{19}$ taken together form a bond,
or a plant physiologically acceptable salt thereof is useful for inhibiting 9-cis-epoxycarotenoid dioxygenase (NCED) in a plant or seed and is therefore useful for regulating ABA biosynthesis in the plant or seed.

14 Claims, 16 Drawing Sheets

U.S. PATENT DOCUMENTS

| | | | |
|---|---|---|---|
| 3,946,078 | A | 3/1976 | Rautenstrauch et al. |
| 4,022,807 | A | 5/1977 | Olson et al. |
| 4,088,681 | A | 5/1978 | Baumann et al. |
| 4,148,829 | A | 4/1979 | Olson et al. |
| 4,219,506 | A | 8/1980 | Olson et al. |
| 4,581,057 | A | 4/1986 | Nooden |
| 4,661,641 | A | 4/1987 | Lukac et al. |
| 5,201,931 | A * | 4/1993 | Abrams et al. ............... 504/291 |
| 5,518,995 | A * | 5/1996 | Abrams et al. ............... 504/348 |
| 5,808,120 | A | 9/1998 | DeLuca et al. |
| 6,004,905 | A * | 12/1999 | Abrams et al. ............... 504/348 |
| 6,100,219 | A | 8/2000 | Sakai et al. |
| 6,372,496 | B1 | 4/2002 | Attree et al. |
| 6,627,795 | B1 | 9/2003 | Coughlan et al. |
| 6,630,615 | B1 | 10/2003 | Bidney et al. |
| 7,098,365 | B2 | 8/2006 | Yoshida et al. |
| 7,119,192 | B2 | 10/2006 | Shinozaki et al. |
| 7,241,937 | B2 | 7/2007 | Fang et al. |
| 7,482,509 | B2 | 1/2009 | Iuchi et al. |
| 2008/0200339 | A1 * | 8/2008 | Abrams et al. ............... 504/313 |

FOREIGN PATENT DOCUMENTS

| | | |
|---|---|---|
| WO | WO 96/38566 | 12/1996 |
| WO | WO 03/020015 | 3/2003 |
| WO | WO 2008/094568 | 8/2008 |

OTHER PUBLICATIONS

Boyd, J. et al. "Towards Specific Inhibitors of 9-cis-Epoxycarotenoid Dioxygenases . . . ". Poster at the Plant Metabolism meeting in Banff, Alberta, Jul. 30, 2008.
Han, S-Y. et al. Plant Physiology. 135:1574-1582, Jul. 2004.
Abe, M. et al. Am. J. Respir. Cell Mol. Biol. 15:565-573, 1996.
Zeevaart, J.A.D. et al. Ann. Rev. Plant Physiol. Plant Mol. Biol. 39:439-473, 1988.
Owen, S.J. et al. "Meaurement of Plant Hormones . . . " in Plant Hormones: Methods and Protocols, 2nd Ed., vol. 495. (Humana Press) Chapter 4, pp. 39-51, 2009.
Livak, K.J., et al. Methods. 25:402-408, 2001.
Walker-Simmons, M., et al. Plant, Cell and Environment. 11:769-775, 1988.
Morris, G.M., et al. Journal of Computational Chemistry. 19(14):1639-1662, 1998.
Guex, N. et al. Electrophoresis. 18:2714-2723, 1997.
Bradford, M.M. Analytical Biochemistry. 72:242-254, 1976.
Guo, S. et al. Biochem. Cell Biol. 86:262-270, 2008.
Rilen, R.W., et al. Plant Physiol. 101:469-476, 1993.
Han, S-y., et al. Bioorganic and Medicinal Chemistry Letters. 12:1139-1142, 2002.
Norris, S.R., et al. Plant Molecular Biology. 21:895-906, 1993.
Yamaguchi-Shinozaki, K. et al. Plant Physiol. 101:1119-1120, 1993.
Cutler, A.J. et al. Biochemistry. 39:13614-13624, 2000.
Huang, D. et al. Journal of Experimental Botany. 59(11):2991-3007, 2008.
Creelman, R.A., et al. Plant Physiol. 77:25-28, 1985.
Schwede, T., et al. Nucleic Acid Research. 31(13):3381-3385, 2003.
Kloer, D.P., et al. Science. 308:267-269, 2005.
Schwartz, S.H., et al. Biochemica et Biophysica Acta. 1619:9-14, 2003.
Furuichi, N. et al., Angew. Chemie Int. Ed. 41(6):1023-1026, 2002.
Nakagawa, I. et al. Tetrahedron Letters. 17:1409-1412, 1975.
Isler, von O., et al. Helvetica Chimica Acta. XXXIX(VII) No. 237, pp. 2041-2053, 1956.
Lamb, N. et al. Can. J. Chem. 68:1151-1162, 1990.
Baumeler, von A., et al. Helvetica Chimica Acta. 73:700-715, 1990.
Kitahata, N. et al. Bioorganic & Medicinal Chemistry. 14:5555-5561, 2006.
Creelman, R.A., et al. Plant Physiol. 99:1258-1260, 1992.
Toh, S., et al. Plant Physiology. 146:1368-1385, 2008.
Nagamune, K., et al. Nature. 451:207-211, 2008.
Endo, A., et al. Plant Physiology. 147:1984-1993, 2008.
Tan, B-C., et al. The Plant Journal. 35:44-56, 2003.
Iuchi, S. et al. Plant Physiology. 123:553-562, 2000.
Chernys, J.T. et al. Plant Physiology. 124:343-353, 2000.
Burbidge, A. et al. The Plant Journal. 17(4):427-431, 1999.
Qin, X. et al. PNAS. 96(26):15354-15361, 1999.
Iuchi, S. et al. The Plant Journal. 27(4):325-333, 2001.
Schwartz, S.H., et al. Science. 276:1872-1874, 1997.
Kushiro, T. et al. The EMBO Journal. 23:1647-1656, 2004.
Milborrow, B.V. The EMBO Journal. 23:1647-1656, 2004.
Nambara, E. et al. Annu. Rev. Plant Biol. 56:165-185, 2005.
McCarty, D.R. Annu. Rev. Plant Physiol. Plant Mol. Biol. 46:71-93, 1995.

* cited by examiner

INHIBITORS OF A 9-CIS EPOXYCAROTENOID DIOXYGENASE

CROSS-REFERENCE TO RELATED APPLICATIONS

This application claims priority to Canadian Patent Application 2,647,900 filed Dec. 23, 2008 and claims the benefit of U.S. Provisional Patent Application Ser. No. 61/193,799 filed Dec. 23, 2008, the entire contents of both of which are herein incorporated by reference.

FIELD OF THE INVENTION

The present application is related to inhibitors of a 9-cis-epoxycarotenoid dioxygenase (NCED), particularly for use in regulating abscisic acid (ABA) biosynthesis in plants and seeds.

BACKGROUND OF THE INVENTION

Abscisic acid (1, ABA) is a plant hormone involved in the regulation of important developmental functions including seed maturation, desiccation tolerance and dormancy, as well as adaptation to environmental stress through stomatal closure and modification of gene expression.[1-3] The biosynthesis of ABA 1 begins with isopentenyl diphosphate which enters the mevalonic acid-independent 2-C-methyl-d-erythritol-4-phosphate pathway producing plastidic isoprenoids, including carotenoids.[4] Enzymatic cleavage of $C_{40}$ carotenoid cis-xanthophylls (neoxanthin 2 and violaxanthin 3) at the 11'-12' double bond by a 9-cis-epoxycarotenoid dioxygenase (NCED) produces $C_{15}$ (xanthoxin 4) and $C_{25}$ metabolites and represents the first committed step in ABA biosynthesis (FIG. 1). Xanthoxin 4 is subsequently converted by an alcohol dehydrogenase (ABA2) into abscisyl aldehyde 5, which is oxidized to ABA 1 by an abscisic aldehyde oxidase (AAO3).[3] The catabolism of ABA occurs principally through oxidation of one of the methyl groups of the ring (8'-carbon atom, using convention for ABA numbering) mediated by members of a class of P450 monooxygenase enzymes, CYP 707A.[5] The catabolite phaseic acid (6, PA) which occurs as the result of reversible cyclization of 8'-hydroxyABA, is reduced by an unknown reductase to afford dihydrophaseic acid (7, DPA). ABA can also be metabolized to the glucose conjugate 8.[3]

First identified in maize (VP14), NCEDs have also been found in a variety of other species including *Arabidopsis thaliana* (AtNCED3), bean (PvNCED1), tomato (LeNCED1), avocado (PaNCED1 and PaNCED3) and cowpea (VuNCED1).[6-11] AtNCED3 is a member of the carotenoid cleavage enzyme family of *Arabidopsis thaliana*, which consists of nine enzymes.[12] In general, the family is characterized by a plastid-targeting transit peptide, an amphipathic α-helix domain and a catalytic domain which contains four conserved histidine residues responsible for non-heme iron co-ordination. AtNCED3 is found in both the stroma and bound to the thylakoid membrane, accounts for NCED activity in roots, contributes to NCED activity in developing seeds and is the major stress-induced NCED in leaves of *Arabidopsis thaliana*.[12] Recently, immunohistochemical analysis revealed that the AtNCED3 protein is detected exclusively in the vascular parenchyma cells of water-stressed plants.[13] Due to ABA's important role in plant physiology, significant effort has been expended on investigating functional aspects of ABA 1 biosynthesis, regulation and action. ABA-deficient mutants are powerful tools for elucidating ABA's role in planta, as are chemical inhibitors of ABA 1 biosynthesis which have broad applicability to many plant species.

General carotenoid biosynthesis inhibitors such as fluridone, a potent broad spectrum herbicide that inhibit phytoene desaturase in the carotenoid biosynthesis pathway, have been used to inhibit ABA 1 biosynthesis.[14,15] While fluridone does inhibit ABA 1 biosynthesis, a corresponding general repression of the carotenoid biosynthesis pathway limits its application for biochemical investigations including those of carotenoid cleavage enzymes and products. To address this problem, Abamine compounds 9 and 10 were developed as inhibitors of NCED's, based on early observations that a number of inhibitors of soybean lipoxygenase were effective in reducing ABA accumulation in stressed soybean cell cultures and seedlings.[16] One of the active compounds, nordihydroguaiaretic acid, served as the starting structure for generation of analogs with improved NCED inhibitory activity, leading to development of the tertiary amines Abamine (9, ABM) and Abamine SG (10, ABM-SG) (FIG. 2).[17,18] *Arabidopsis* plants treated with ABM 9 showed a significant decrease in drought tolerance and under simulated osmotic stress ABM 9 inhibited stomatal closure in spinach leaves. The latter effect was counteracted by co-application of ABA 1. ABM-SG 10 strongly inhibited the expression of ABA-responsive and catabolic genes in plants under osmotic stress. Finally, both ABM 9 and ABM-SG 10 reduced ABA metabolite accumulation by 35% and 77% respectively and were shown to act as competitive inhibitors of the cowpea NCED enzyme, with Ki's of 18.5 μM and 38.8 μM respectively.

There remains a need for NCED inhibitors for use in regulating ABA biosynthesis in plants.

SUMMARY OF THE INVENTION

There is provided a compound of formula (I):

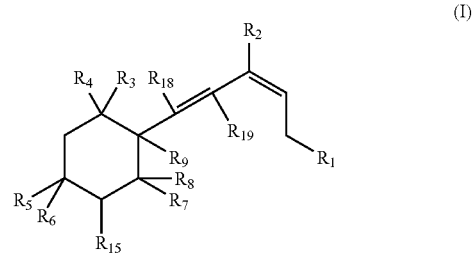

wherein:
$R_1$ is —$SR_{10}$, —O—C(O)—$R_{11}$, —$NR_{12}R_{13}$, where $R_{10}$ is a $C_{1-8}$-alkyl group or a phenyl group unsubstituted or substituted by a $C_{1-4}$-alkyl group, $R_{11}$ is a thiophenenyl, furanyl or pyrrolyl group, $R_{12}$ is H or a $C_{1-4}$-alkyl group and $R_{13}$ is a $C_{1-8}$-alkyl group or a phenyl group unsubstituted or substituted by a $C_{1-4}$-alkyl group;
$R_2$ is H or a $C_{1-4}$-alkyl group;
$R_3$ and $R_4$ are independently H or $C_{1-4}$-alkyl groups;
$R_5$ and $R_6$ are independently H, OH or $OR_{14}$, or taken together are =O, where $R_{14}$ is a protecting group;
$R_7$ is H or a $C_{1-4}$-alkyl group;
$R_8$ is H, $R_9$ is OH and $R_{15}$ is H, or $R_{15}$ is H and $R_8$ and $R_9$ taken together are —O—, or $R_9$ is OH and $R_8$ and $R_{15}$ taken together form a bond; and,
$R_{18}$ and $R_{19}$ are both H, or $R_{18}$ and $R_{19}$ taken together form a bond,
or a plant physiologically acceptable salt thereof.

Preferably, $R_{10}$ is ethyl or phenyl. Preferably, $R_{11}$ is thiophenenyl. Preferably, $R_{12}$ is H. Preferably, $R_{13}$ is phenyl. Preferably, $R_1$ is —$SR_{10}$. Preferably, $R_2$ is methyl. Preferably, $R_3$ is methyl. Preferably $R_4$ is methyl. Preferably, one of $R_5$ and $R_6$ is OH or $R_5$ and $R_6$ taken together are =O. Preferably, $R_7$ is methyl. Preferably, $R_{15}$ is H. Preferably, $R_{18}$ and $R_{19}$ taken together form a bond.

Plant physiologically acceptable salts are generally known in the art and include, for example, acetates, hydrochlorides, sulfates.

Compounds of the present invention may be synthesized in accordance with a process as illustrated in Scheme 1:

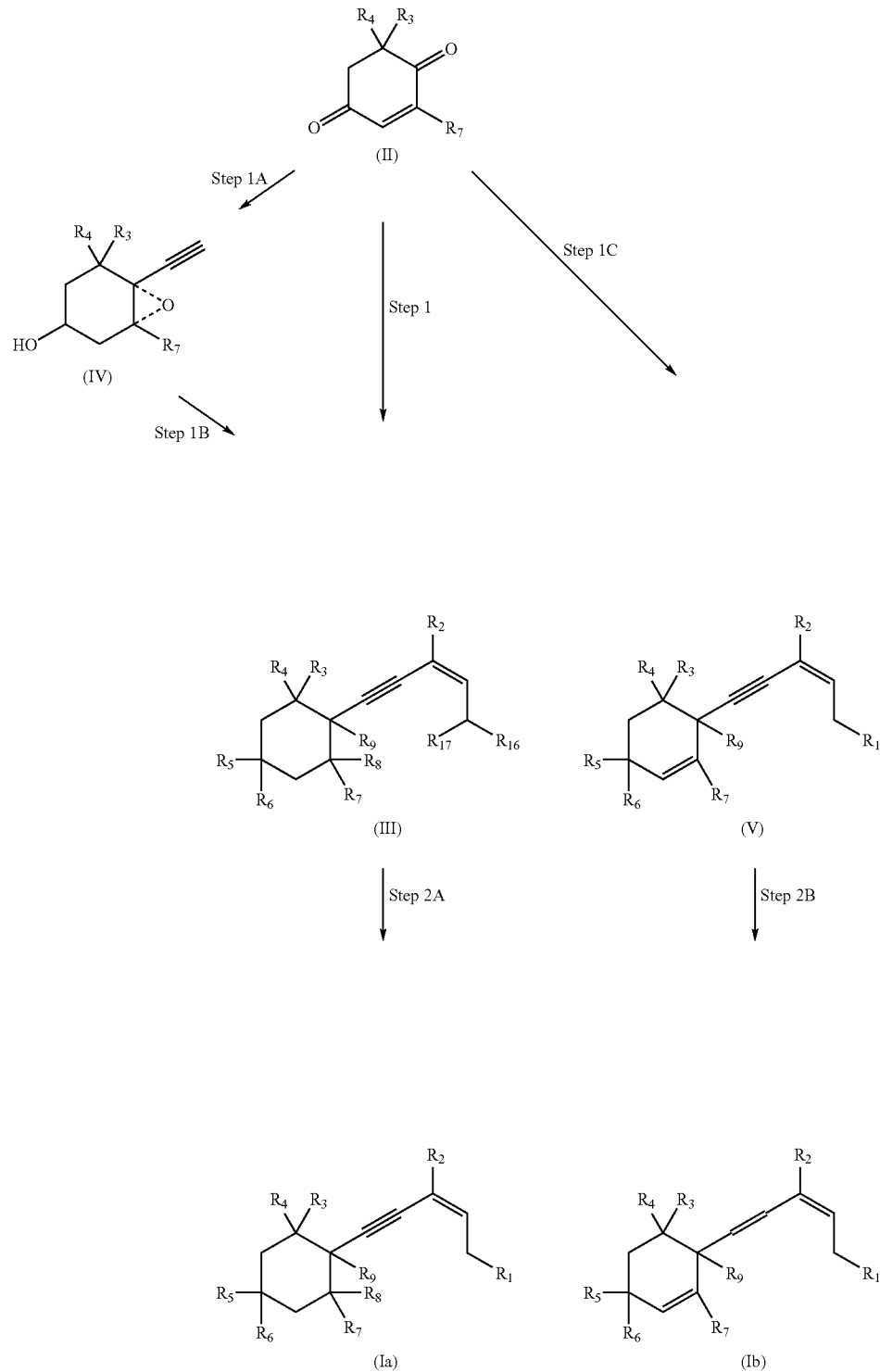

wherein $R_1$, $R_2$, $R_3$, $R_4$, $R_5$, $R_6$, $R_7$, $R_8$ and $R_9$ are as defined above; and $R_{16}$ is OH and $R_{17}$ is H, or $R_{16}$ and $R_{17}$ taken together are =O.

Referring to Scheme 1, in Step 1 allylic compounds (III) where $R_9$ is OH may be prepared from 4-oxoisophorones (II) by initial reduction of (II) followed by conversion of the resulting 1,4-diones to allylic alcohols (III) by known methods.[20] Reduction may be accomplished by any suitable means, for example by Baker's yeast reduction or with an appropriate reducing metal (e.g. zinc in acetic acid). Alternatively, allylic compounds (III) where $R_8$ and $R_9$ taken together are —O— may be prepared from 4-oxoisophorones (II) by an initial multi-step synthesis (Step 1A[22]) to yield allylic epoxide (IV) followed by conversion of (IV) to (III) (Step 1B) by condensing (IV) with a 3-iodobut-2-en-1-ol. The condensation of (IV) with 3-iodobut-2-en-1-ol is preferably performed in the presence of a catalyst. Compounds of formula (III) where $R_{16}$ is OH and $R_{17}$ is H may be converted to compounds of formula (III) where $R_{16}$ and $R_{17}$ taken together are =O by oxidation, for example with $MnO_2$. The protecting group, $R_{14}$, may be any suitable protecting group known in the art, for example, t-butyldimethylsilyl (TBDMS) or t-butyldiphenylsilyl (TBDPS).

Conversion of (III) to (Ia) (Step 2A), where (Ia) represents a sub-set of compounds of formula (I), may be accomplished by condensing (III) with $R_1L$, where L is a leaving group. This condensation is preferably performed in the presence of a base (e.g. tributylphosphine, triethylamine) when $R_{16}$ is OH, or with subsequent action of a reducing agent (e.g. sodium borohydride) when $R_{16}$ and $R_{17}$ taken together are =O. The leaving group may be, for example, H, halogen (e.g. Cl, Br), tosylate, brosylate or a second unit of $R_1$.

Compounds (Ib), another sub-set of compounds of formula (I) where the allylic bond has been hydrogenated to an olefinic bond, may be formed from (II) (Step 1C and Step 2B). Thus, (II) may be converted to (V) in Step 1C by known methods[20] as indicated above for Steps 1 and 2A without the initial reduction of (II) to the 1,4-dione, followed by reduction of the allylic bond to an olefinic bond in Step 2B using $H_2$ and an appropriate catalyst (e.g. Pd, Pd—$CAaCO_3$—PbO) or by using diisobutlyaluminum hydride.

If required or desired, deprotection to yield the corresponding hydroxy may be accomplished by generally known methods, for example by the action of tetra-n-butylammonium fluoride (TBAF). Compounds may be converted to salts by reaction with a suitable acid or base.

Compounds and salts thereof of the present invention are useful for inhibiting 9-cis-epoxycarotenoid dioxygenase (NCED) in plants. In particular, they are useful for regulating abscisic acid (ABA) biosynthesis in plants. More particularly, they are useful for regulating seed maturation, desiccation tolerance, dormancy and adaptation to environmental stress through stomatal closure and modification of gene expression in plants. Environmental stress includes abiotic stress (e.g. heat, cold, alkalinity, acidity) and biotic stress (e.g. pathogens).

Thus, in one embodiment of the present invention, there is provided a method of inhibiting 9-cis-epoxycarotenoid dioxygenase (NCED) in a plant or seed comprising administering to the plant or seed a 9-cis-epoxycarotenoid dioxygenase inhibiting effective amount of a compound of formula (I) or a plant physiologically acceptable salt thereof. The method preferably comprises identifying whether the plant is in need of 9-cis-epoxycarotenoid dioxygenase (NCED) inhibition.

Compounds or salts thereof of the present invention may be applied directly to plants or seeds or formulated into compositions for administration to plants or seeds. Compositions may comprise, for example, common plant physiologically acceptable carriers, excipients, diluents and/or nutrients, for example, water, buffers, sugars, salts, vitamins, etc. Advantageously, the compounds or salts thereof may be administered to the plants or seeds by inclusion in a growth medium on which the plant or seed grows, or by spraying the plants or seeds with the compound, a salt thereof or a composition thereof. The compounds or salts thereof may be administered in a suitably effective amount to inhibit NCED. Concentrations of 0.25 µM or more in the application medium are generally suitable. Compounds, salts thereof or compositions thereof may be packaged into a commercial package together with instructions for use.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
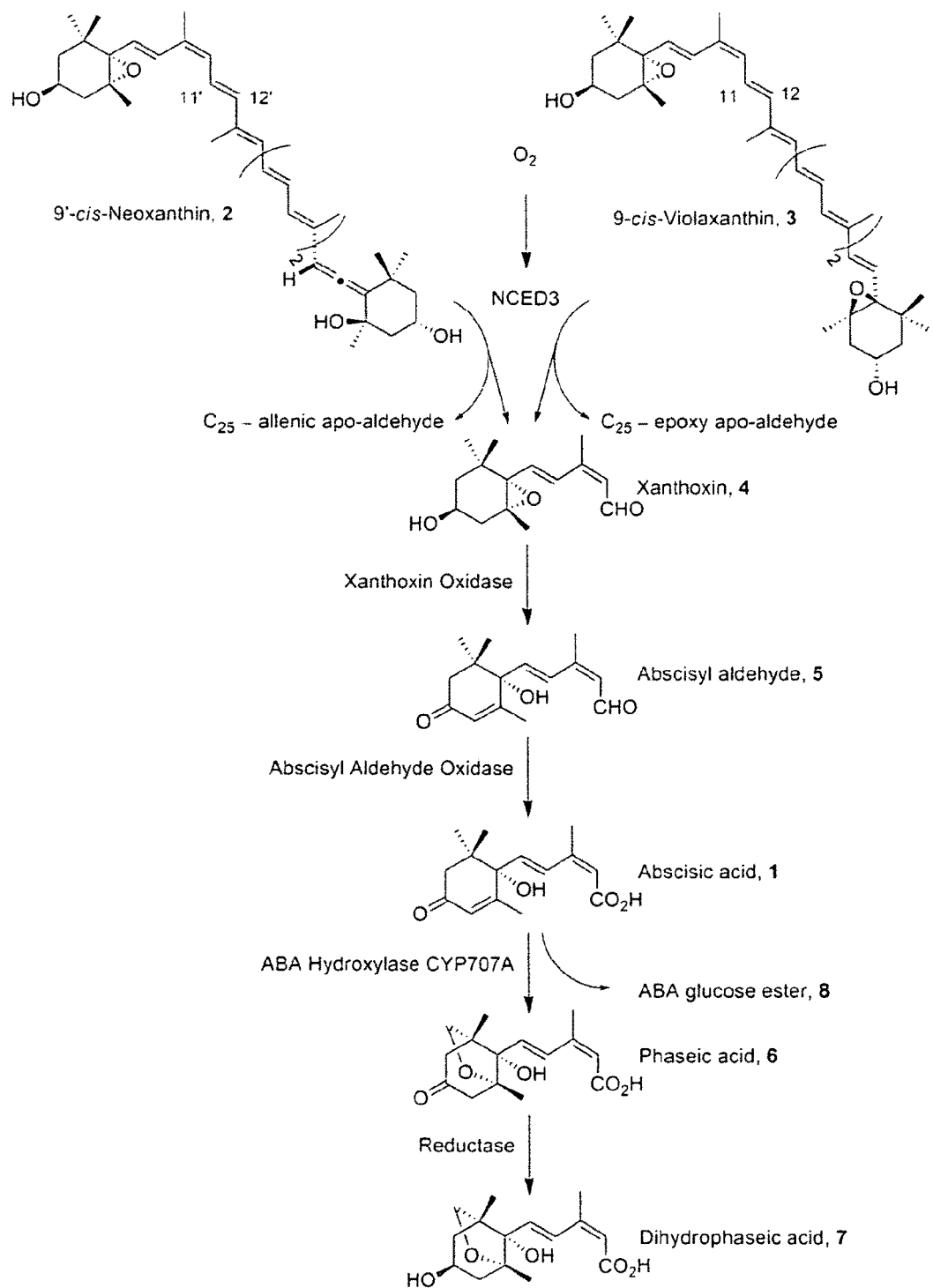
FIG. 1. ABA biosynthesis and catabolism pathway of higher plants from the committed step of $C_{40}$-carotenoid cleavage of either 9-cis-neoxanthin 2 or 9-cis-violaxanthin 3 by AtNCED3.
Figure 2:
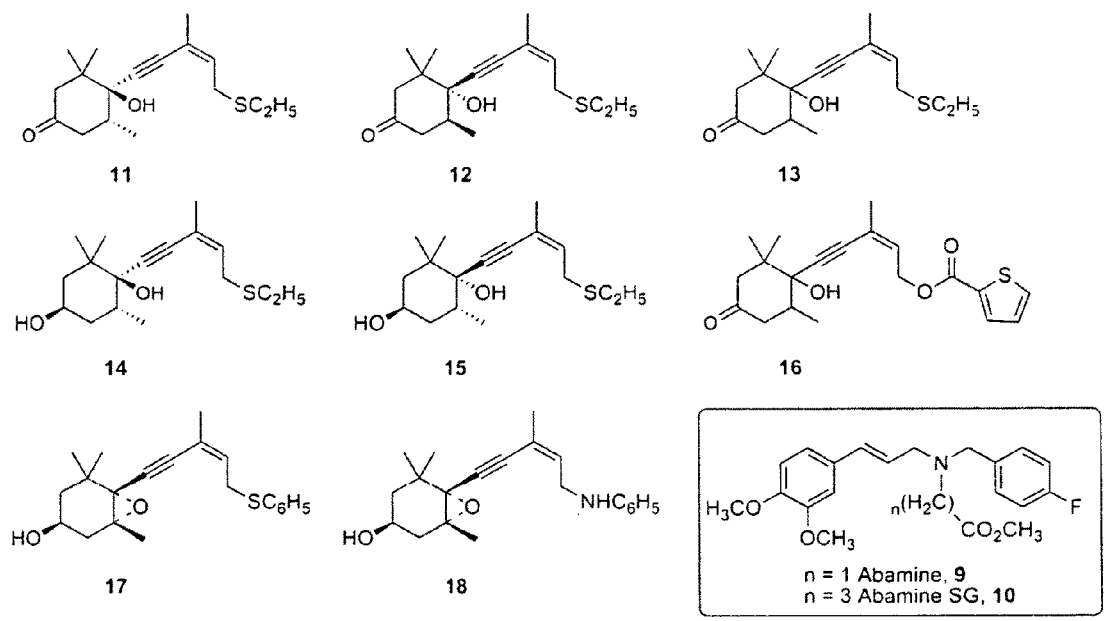
FIG. 2. Structures of AtNCED3 SLCCD inhibitors.

In preferred embodiments, the design, synthesis and characterization of novel sesquiterpene-like carotenoid cleavage dioxygenase (SLCCD) inhibitors 11-18 (FIG. 2) are described below. These novel compounds were designed starting with the sesquiterpenoid subunit of the substrate and product of the NCED enzyme. Of these inhibitors, three were found to inhibit recombinant AtNCED3 activity more strongly. These have been fully characterized in vitro, with kinetic inhibition constants comparing favorably to those of the ABM-type compounds. Computational docking of the inhibitors correlated with these findings and supported the proposed functional mechanism. In vivo, one inhibitor in particular, SLCCD inhibitor compound 13 was found to moderate ABA responsive genes and ABA metabolism. Interestingly, the inhibitors reduced expression of AtNCED3, presenting a second mechanism for inhibition of ABA 1 biosynthesis by the molecules.

While in vitro studies identified SLCCD compound 17 as the most promising candidate inhibitor, hormone profiling data convincingly demonstrated that SLCCD 13, a more easily synthesized racemic compound, best met the objective of reducing the total ABA metabolite levels in planta. Overall, these sesquiterpenoid-like inhibitors present new tools for controlling and investigating ABA biosynthesis, regulation and effects.

Methods:

AtNCED In Vitro Assay Substrate Preparation

Fresh spinach was macerated under liquid nitrogen and extracted five times with three volumes of methanol/0.1% KOH. Samples were dried using a roto-evaporator, resuspended in acetone and then chilled on ice for one hour. The solvent was subsequently transferred to a new flask, roto-evaporated and resuspended in acetonitrile/acetone (1:1) mixture. The mixture was applied to a gravity flow column containing C-18 silica gel (Sigma) equilibrated in 65% acetonitrile/35% water (solvent C). The column was washed with 49% acetone (solvent D)/51% solvent A and 20 mL of 55% solvent D/45% solvent A while collecting 5 mL fractions. Fractions containing neoxanthin were pooled, dried, and resuspended in 100 µL of methanol. The pooled mixture was separated using an Agilent 1100 series HPLC and a Supelcosil™ LC-18 (25 cm×10 mm, 5 m) (Supelco) column equilibrated with solvent A. The HPLC method consisted of a linear gradient over 30 minutes from 100% solvent A to 100% solvent D with a flow rate of 4 mL/minute at 22° C. and monitored with a PDA detector at 436 nm. The neoxanthin fractions were collected, dried and resuspended in ethanol. Neoxanthin was quantified by determining its OD439 using a PerkinElmer Lambda 35 UV/VIS Spectrometer and applying its extinction coefficient of 2243 ($A^{1\%}_{1cm}$).[30]

Recombinant AtNCED3 Expression, Purification and In Vitro Assays

AtNCED3 was over-expressed using the pRL296 expression vector (a gift from M. Cygler, BRI, Montreal) in E. coli (BL21)DE3 cells as a glutathione-S-transferase fusion protein and affinity purified using glutathione sepharose 4 fast flow resin (GE Healthcare) as described previously.[35] Essentially, cells were grown to an OD600 of 0.45 at 37° C. and 200 rpm shaking. The culture was induced with 1 mM isopropyl-β-d-thiogalactoside for 16 h at 15° C. and 200 rpm shaking. The cells were pelleted and resuspended in 50 mM Tris-HCl (pH 8.0) 1 mM DTT and 0.5% protease inhibitor cocktail set III (CalBiochem). Cells were lysed using a french press at 20,000 psi and affinity purified as per manufacturer's instructions (GE Healthcare). Protein concentration was determined by the method of Bradford.[36]

Enzymatic assays contained 100 mM Bis-Tris (pH 6.7), 5 M FeSO$_4$, 10 mM ascorbate, 0.05% Triton™ X-100, catalase (1 mg/mL), neoxanthin and inhibitor to a total volume of 5 L of ethanol and 8 g AtNCED3 to a total assay volume of 100 L. Assays were incubated at 22° C. for 20 min. The assays were stopped with the addition of 50 L of 25% Triton™ X-100 and extracted with 150 L of ethyl acetate. All procedures were performed under red-light to minimize photo-induced damage to assay components and products.[6] Fine chemicals and solvents were purchased from Sigma-Aldrich. 75 µL of the assay extract was injected into an Agilent 1100 series HPLC machine equipped with a Supelcosil™ LC-18 (3.3 cm×4.6 mm, 3 m) (Supelco) column pre-equilibrated with 15% acetonitrile (solvent B)/85% water (solvent A). Solvent B increased to 35% over ten minutes, followed by a linear gradient of 65% solvent B to 100% solvent D over 10 minutes. Solvent D was maintained at 100% for 2 minutes and then the column was returned to 15% solvent B for 5 min. The flow rate was maintained at 1.5 mL/min. and monitored with a photodiode array (PDA) detector at 436 and 262 nm.

Evaluation of recombinant AtNCED3 kinetic parameters for $K_m$ was accomplished using Michaelis-Menten equation plotted with EnzFitter™ v2.0.18.0 (Biosoft). The $K_i$ for inhibitors was determined using a Dixon plot and concentration ranges of 250, 200, 150, 100, 50 and 0 µM inhibitor in the presence of either 55, 30 or 10 µM 9-cis-neoxanthin 2.[5]

Homology Modeling of AtNCED3

A homology model of AtNCED3 was built using the X-ray crystal structure of *Synechocystis* sp. PCC 6803 ACO (pdb code: 2biw; available at the RCSB Protein Data Bank) at 2.39 Å resolution as a structural template.[25] To model AtNCED3, amino acid alignments were made between ACO, AtNCED3 and VP14. AtNCED3 shares 25% and 45% amino acid identity and similarity with ACO, and 64% and 76% respectively with VP14.[37] Highly conserved amino acids including H183, H238, H304 and H484 forming the octahedral coordination of the non-heme iron required for catalysis of the dioxygenase reaction were used to aid in development of a suitable alignment and ultimately build the homology model. Homology modeling jobs were submitted to the Swiss-Model servers using the DeepView program as an interface.[26] Each generation of the AtNCED3 homology model was energy minimized within DeepView using 1000 steps of steepest descent followed by 1000 steps of conjugate gradient minimization until the RMS gradient of the potential energy was less than 0.01 kJ.

In Silico Docking of AtNCED3 Active Site SLCCD Inhibitor Interactions

Inhibitor structures were created using CS ChemOffice™ v9 (CambridgeSoft). In silico docking of inhibitor structures to the AtNCED3 homology model were performed using AutoDock™ v3.1 on a Silicon Graphics Octane2 Workstation.[38] Inhibitor structures were docked within a grid box encompassing the entire catalytic pocket of AtNCED3 corresponding to 80×36×30 points using a spacing of 0.375 Å between grid points. The docking parameters consisted of 20 Lamarckian Genetic Algorithm runs using a population size of 100 individuals and 1,000,000 energy evaluations. Final docked structures having orientations less than or equal to 0.5 Å root mean square deviation were clustered.

In Vivo Application of SLCCD Inhibitors to *Arabidopsis thaliana* Col-0

For each condition to be tested, three hundred wild-type *Arabidopsis thaliana* Col-0 seeds (LEHLE) were sterilized, vernalized and sewn onto 200 mL of Sunshine Mix #3 (Sun Gro) potting material in an 8×8×4 cm pot. Plants were watered continuously with 25 g/100 mL of 20-20-20 (Plant-Prod™) fertilizer and grown at 22° C. with a 16 hour photoperiod for 22 days. Plants were pre-treated with 50 mL/pot of Buffer A (10 mM HEPES pH 6.5) (Sigma)+/−10 or 33 µM test compound for 2 hours. Plants were then soaked with 50 mL/pot of Buffer A containing 0.4 M mannitol (Sigma)+/−10 or 33 µM test compound. Non-treated/non-stressed control plants were simply soaked in Buffer A at the designated time points. Aerial plant tissue was harvested after 6, 12 and 48 hours from the time of initial inhibitor treatment and flash frozen in liquid nitrogen. Half of the tissue samples were lyophilized for metabolite profiling and the other half taken for quantitative reverse-transcription polymerase chain reaction (qRT-PCR) analysis.

Metabolite Profiling of *Arabidopsis thaliana* Hormone Levels

Freeze-dried tissue was homogenized using a multi-tube ball mill (Mini-BeadBeater-96™, Biospec Products Inc., Bartlesville, Okla., USA) and 50 mg of each sample was weighed out into individual Falcon tubes. To each sample, 100 µL of a cocktail of internal standards comprised of (−)-5,8',8',8'-d4-ABA, (−)-7',7',7'-d3-PA, (−)-5,8',8',8'-d4-7'OH ABA, (−)-7',7',7'-d3-DPA and (+)-4,5,8',8',8'-d5-ABAGE, each at a concentration of 0.2 ng/µL and dissolved in a mixture of water:acetonitrile (1:1, v/v) with 0.5% glacial acetic acid, was added. Further, 3 mL of isopropanol:water:glacial acetic acid (80:19:1, v/v/v) extraction solvent was added, and samples were placed in the fridge (4° C., in the dark) on an orbital shaker at about 350 rpm. After 18-24 hours, the samples were centrifuged at 4.4 krpm for 10 min, the supernatant was transferred to a disposable culture tube, and a second portion of 500 µL extraction solvent mixture was added to wash the pellet. After vortexing and centrifuging again at 4.4 krpm for 10 min, each wash was combined with its appropriate supernatant. The organic extract was dried under reduced pressure, then re-dissolved in 100 µL methanol:glacial acetic acid (99:1, v/v) followed by 900 µL of aqueous 1% glacial acetic acid. This mixture was extracted with 2 mL hexane, and then the aqueous layer was dried down under reduced pressure. The sample was further reconstituted in 2 mL aqueous 1% glacial acetic acid and loaded onto an Oasis MCX SPE cartridge (3 cc, Waters Corporation, Mississauga, Ontario, Canada). After a wash with 3 mL aqueous 1% glacial acetic acid, samples were eluted with 1 mL methanol: glacial acetic acid (99:1, v/v) and then dried down under reduced pressure. The extract was re-dissolved in 100 µL methanol:glacial acetic acid (99:1, v/v) followed by 900 µL of aqueous 1% glacial acetic acid. This mixture was further cleaned on an Oasis HLB SPE cartridge (1 cc, Waters Corporation, Mississauga, Ontario, Canada). After a wash with 1 mL aqueous 1% glacial acetic acid, the fraction containing ABA and ABA metabolites was eluted with 1 mL acetonitrile: water:glacial acetic acid (30:69:1, v/v/v) and then was evaporated to dryness. The final residue was dissolved in 200 µL of acetonitrile:water (15:85, v/v) containing 0.1% glacial acetic acid and 100 pg/µL (±)-3',5',5',7',7',7'-d6-ABA as a recovery standard. Finally, the sample was subjected to LC-ES-MS/MS analysis and quantification, as described in Owen and Abrams, 2008.[39]

Seed Germination Assay

*Arabidopsis thaliana* Col-0 seeds were sterilized by washing them with 10% sodium hypochlorite and 20% sodium dodecyl sulfate (Sigma) for five minutes and then rinsing four times with sterile water. Seeds were moist chilled for 4 days and then plated on germination medium (0.41% MS salts, 1% sucrose, 0.05% MES and 0.1% Gamborg's vitamins, pH 5.7, 0.7% agar) (Sigma) containing either 0.1, 0.33, 1.0 or 3.33 µM of inhibitor or (+)-ABA 1. As a control, seeds were sewn and germinated on media only without inhibitors or (+)-ABA 1. Germination was recorded over seven days and indexes calculated as described previously.[40]

Quantitative Reverse-Transcription PCR (qRT-PCR)

250 mg of frozen plant material was ground under liquid nitrogen and extracted for mRNA as suggested by the manufacturer (PolyATract™ System 1000, Promega). The resulting mRNA was quantified and checked for quality using a Nano-Drop™ ND-1000 Spectrophotometer. QuantiTect™ Reverse Transcription Kit (Qiagen) was used to produce cDNA as directed by the manufacturer from 20 ng of starting mRNA. Quantitative PCR was performed on 1 µL of cDNA product using a Bio-Rad iCycler™ and the QuantiTect™

SYBR Green PCR Kit (Qiagen) coupled with QuantiTect™ Primer Assays (Qiagen) for the gene targets; AtNCED3 (NM_112304), Rd29B (NM_124609), CYP707A1 (NM_118043), CYP707A3 (NM_123902) and UBQ10 (NM_178968). The pre-validated primer sets are as follows indicated by the GeneGlobe (www1.qiagen.com/GeneGlobe/default.aspx) product name and (catalogue number): At_NCED3_1_SG (QT00769573), At_RD29B_1_SG (QT00840399), At_CYP707A1_1_SG (QT00808339), At_CYP707A3_1_SG (QT00739242), At_UBQ10_va.1_SG (QT01123745). Relative changes in transcript level were normalized using UBQ10 and quantified as previously described.[41]

Results:

Design and Synthesis of the SLCCD Inhibitors

Figure 3:
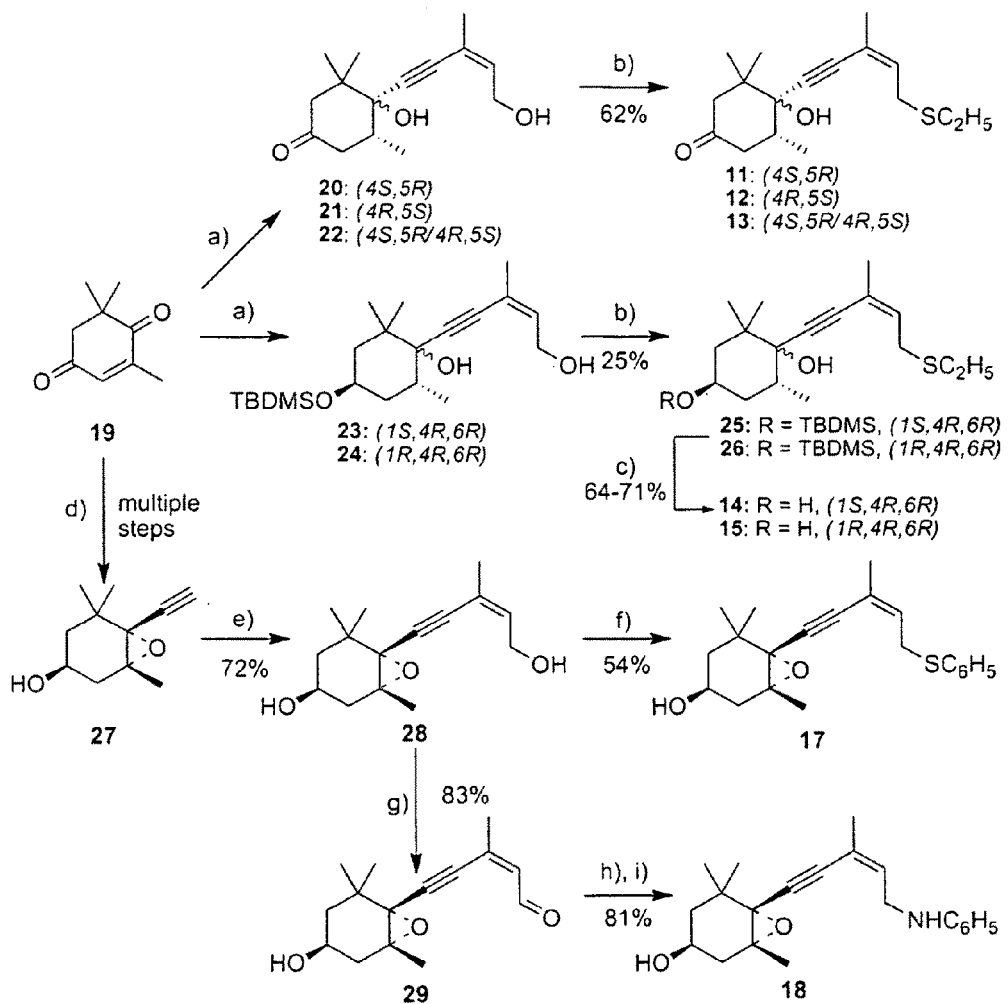
FIG. 3. Synthesis of AtNCED3 SLCCD inhibitors. a) See reference[20]; b) n-$Bu_3P$, $(C_2H_5S)_2$; c) TBAF, THF; d) See reference[22] e) (Z)-3-iodobut-2-en-1-ol, $(Ph_3P)_4Pd$, CuI, $(i-Pr)_2NH$; f) n-$Bu_3P$, $(C_6H_5S)_2$; g) $MnO_2$; h) $C_6H_5NH_2$, Δ; i) $NaBH_4$.

The present compounds were designed to incorporate the 9-cis double bond geometry of the substrates and product of AtNCED3 as well as a heteroatom at carbon 12 (carotenoid numbering) of the inhibitor molecules. All of the SLCCD inhibitors 11-18 were synthesized from 4-oxoisophorone 19 (FIG. 3). Bakers' yeast reduction of 19 afforded (−)-(R)-2,2,6-trimethylcyclohexa-1,4-dione[19] which was converted into chiral nonracemic allylic alcohols 20, 21, 23 and 24.[20] Racemic allylic alcohol 22 was prepared in a similar manner, except that reduction of 19 was accomplished using zinc in acetic acid.[21] The terminal allylic alcohols were then converted to the corresponding ethyl sulfides by reaction with ethyl disulfide in the presence of tributylphosphine.[22] Inhibitor 16 was obtained by reacting 2-thiopheneacetyl chloride and allylic alcohol 22 (protected as the neopentylglycol ketal). The xanthoxin-like allylic alcohol 22 was prepared through a Sonogashira coupling between the terminal acetylene in 21[23] and (Z)-3-iodobut-2-en-1-ol. Alcohol 22 was then converted to the phenyl sulfide 13 with 54% yield. The nitrogen-containing inhibitor 18 was synthesized by oxidation of allylic alcohol 22 with $MnO_2$, followed by imine formation using phenyl amine and then reduction to the amine.

In Vitro Assays and Kinetic Analyses

Figure 4:
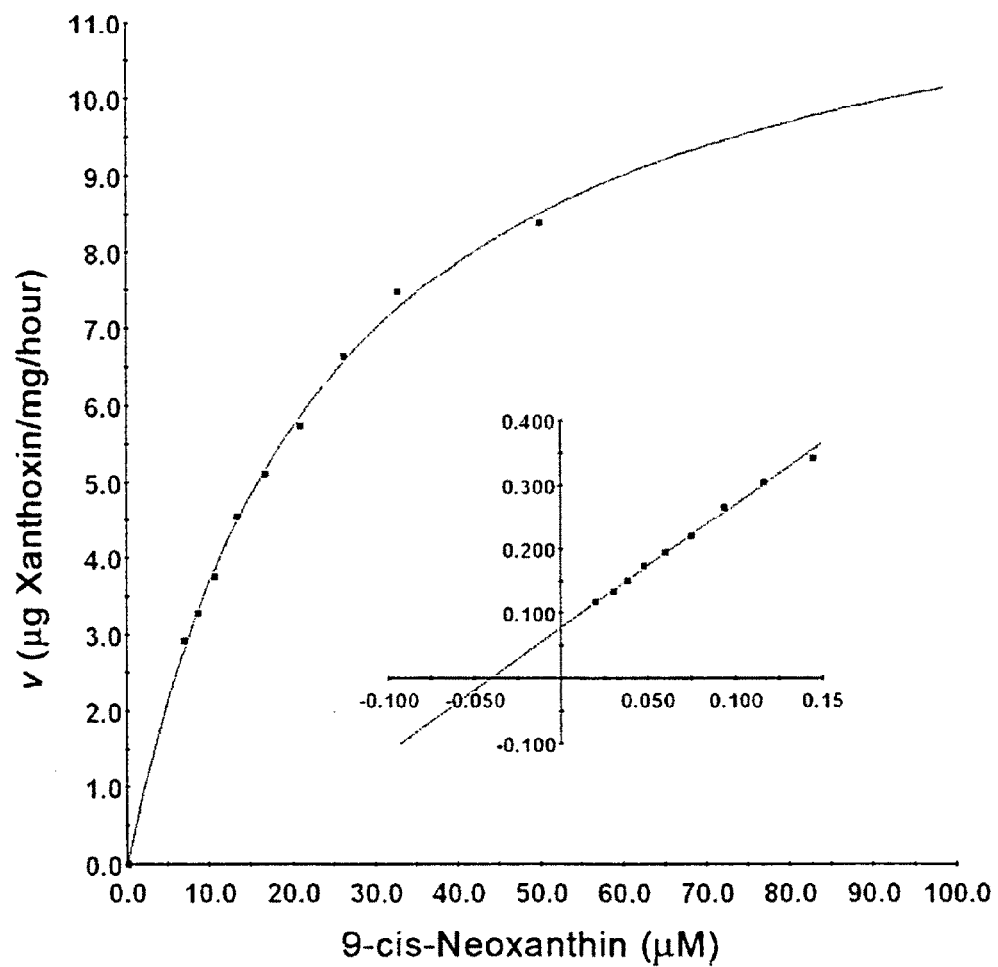
FIG. 4. Kinetic analysis of recombinant purified AtNCED3 activity. Michaelis-Menton plot for cleavage of 9-cis-neoxanthin 2 by recombinant AtNCED3 indicating a $K_m$ of 24 µM.
Figure 10:
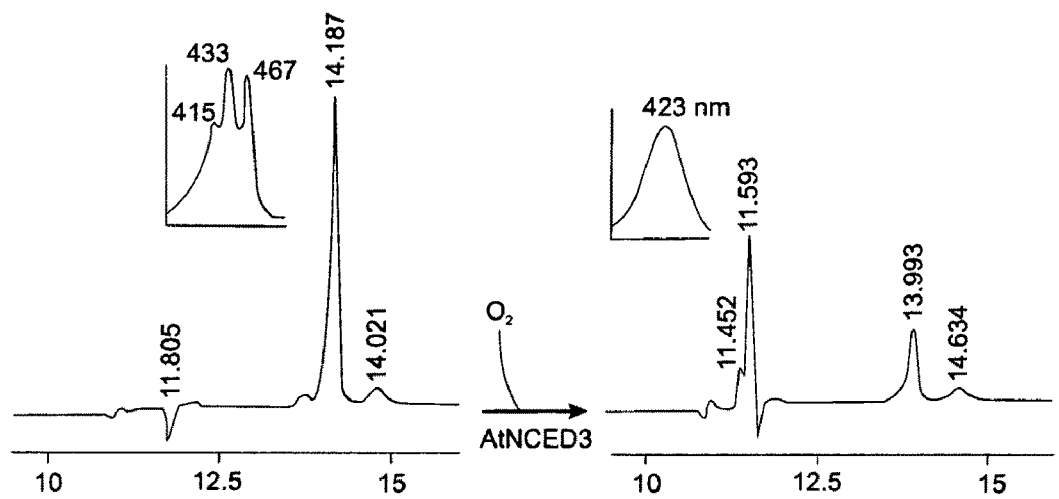
FIG. 10. HPLC profiles showing substrate (left panel) and product (right panel) for AtNCED3 in vitro reactions. The substrate 9-cis-neoxanthin peak is observed at 14.187 minutes with three maxima at 415, 438 and 467 nm and the $C_{25}$-allenic apo-aldehyde cleavage product observed at 11.593 minutes with a maxima of 423 nm.

Recombinant AtNCED3 including a C-terminally located glutathione-S transferase fusion tag was expressed in *E. coli* and purified by affinity chromatography. In vitro assays demonstrated the functionality of the recombinant purified enzyme product. Sample HPLC profiles (FIG. 10) show cleavage of the 9'-cis-neoxanthin 2 substrate ($R_t$ 14.2 min. with three maxima at 415, 438 and 467 nm) producing the expected $C_{25}$-allenic apo-aldehyde cleavage product ($R_t$ 11.6 min. with a maxima of 423 nm). Further kinetic analysis fitted by non-linear regression analysis defined a $K_m$ of 24 µM (FIG. 4). This value correlates well with the $K_m$'s of 27 µM and 49.0 µM determined previously for VP14 and VuNCED1.[18,24]

Figure 5:
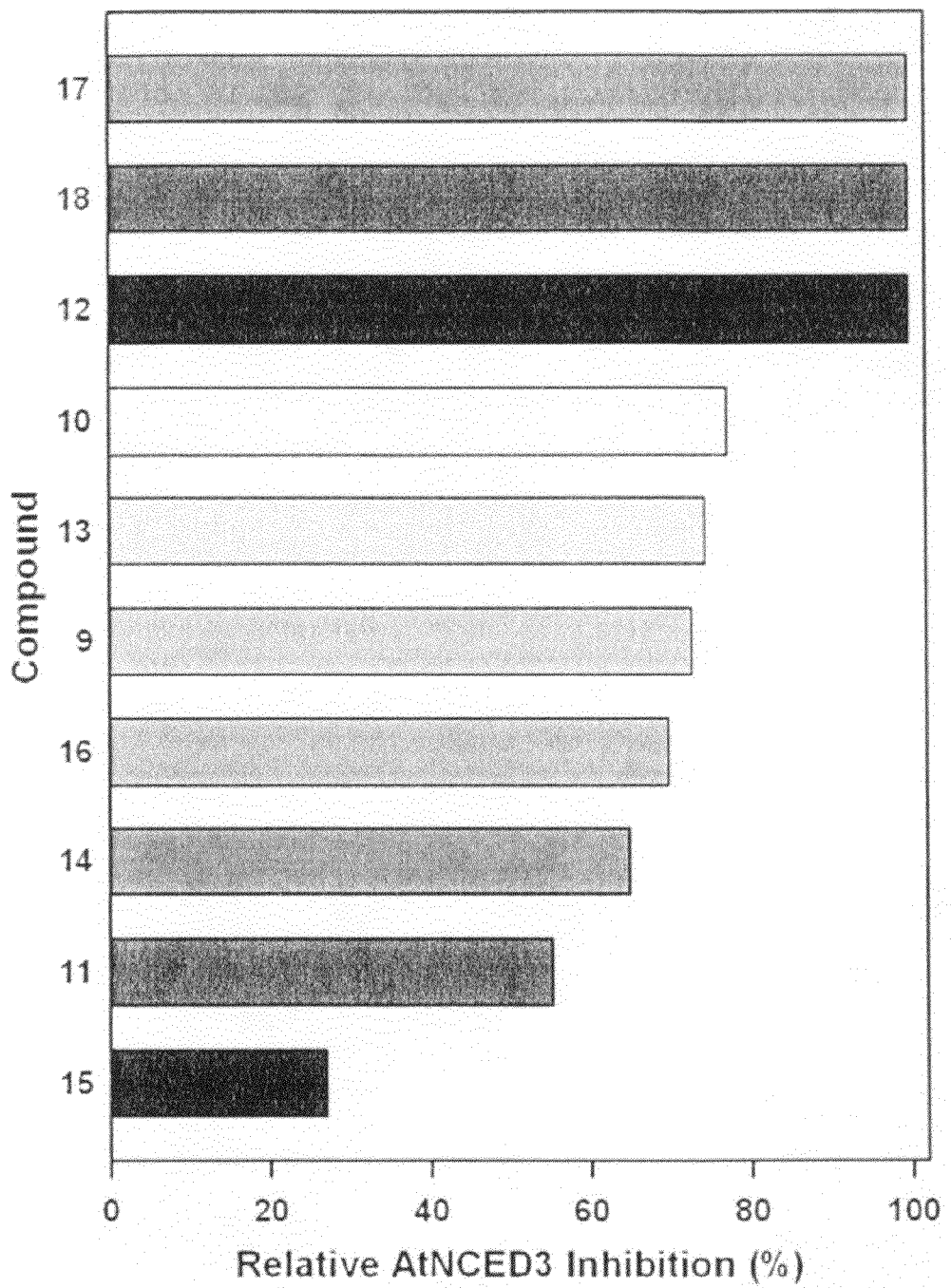
FIG. 5. Relative inhibition of recombinant AtNCED3 activity by various SLCCD compounds at 1 mM concentration.
Figure 11:
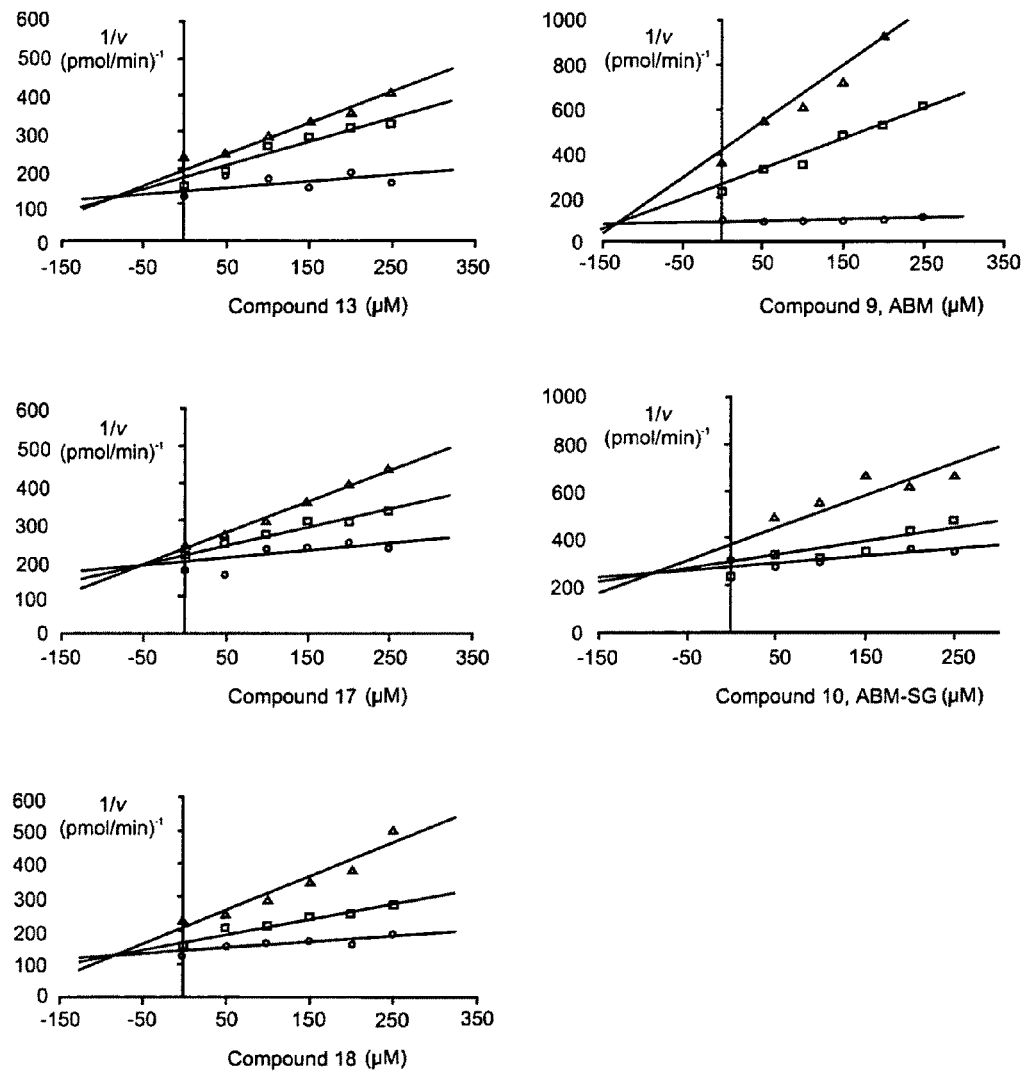
FIG. 11. Inhibition kinetic Dixon plot analyses of recombinant AtNCED3 activity measured in the presence of 50 µM (diamonds), 30 µM (squares) and 10 µM (triangles) 9-cis-neoxanthin, with compounds 9, 10, 13, 17 and 18 at the indicated concentrations. $K_i$ values are reported in Table 1.

Using this recombinant enzyme and assay system, the eight potential inhibitor compounds were tested for their relative ability to inhibit AtNCED3 activity at 1 mM concentration (FIG. 5). Compounds 12, 17 and 18 completely inhibited AtNCED3 activity at 1 mM, while 13 inhibited AtNCED3 activity by 75%. Compound 12 is one of the stereoisomers of racemic 13. The latter being easier to synthesize (and thus of higher potential practical application), it was decided to move forward with compounds 13, 17 and 18 for detailed in vitro and in vivo testing. Dixon plots indicated that compounds 13, 17 and 18 competitively inhibit recombinant AtNCED3 with $K_i$'s comparable or better than those observed for ABM and ABM-SG (Table 1 and FIG. 11).

TABLE 1

| Compound | $K_i$ (µM) | $K_m$ (µM) |
|---|---|---|
| 2 (9-cis-Neoxanthin) | — | 24 |
| 13 | 93 | — |
| 17 | 57 | — |
| 18 | 87 | — |
| 10 (ABM-SG) | 86 | — |
| 9 (ABM) | 132 | — |

Homology Modeling and SLCCD Inhibitor Docking

Figure 6:
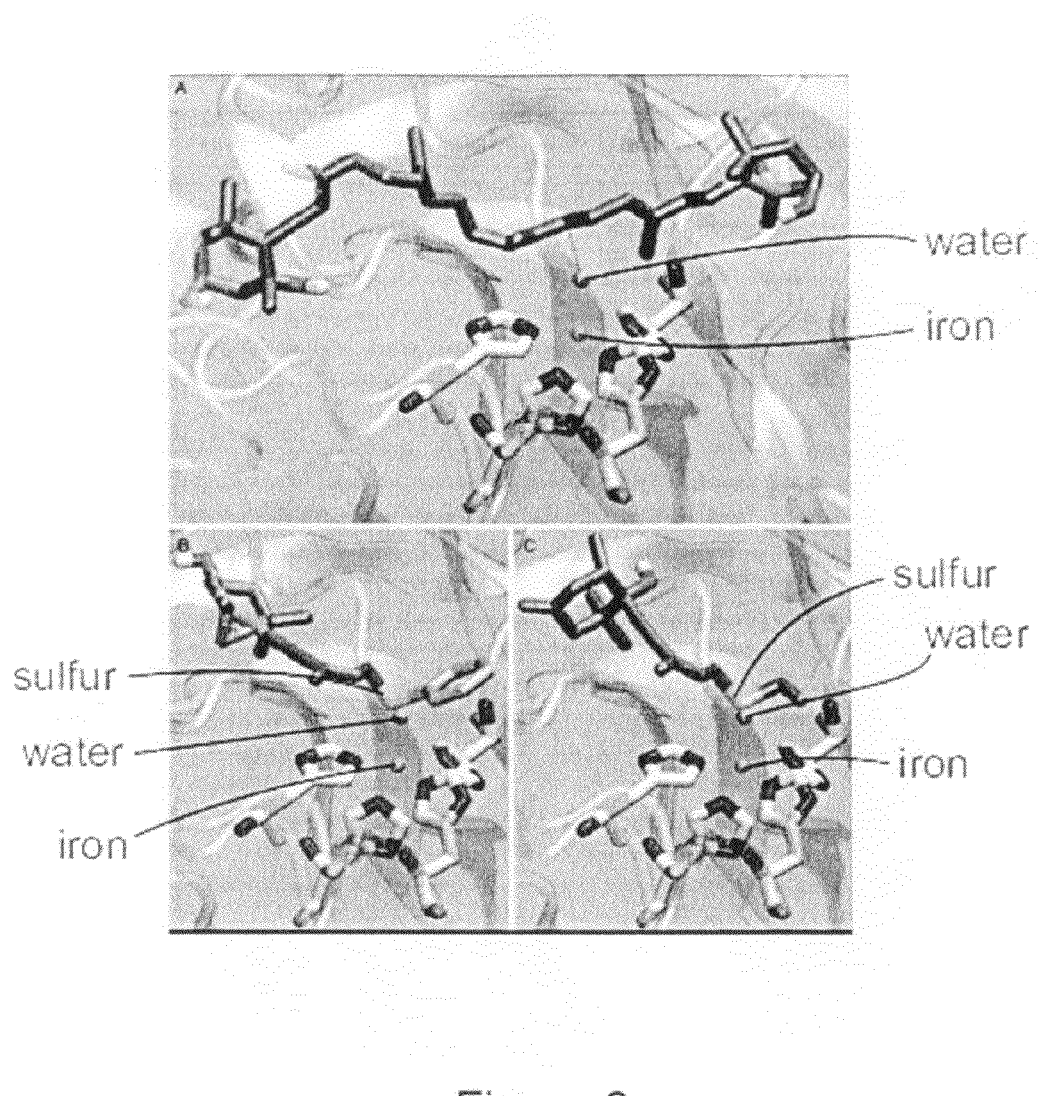
FIG. 6. Computational docking of compounds to the AtNCED3 homology model. Docking was performed using the Autodock v3.1 software.[38] Conserved histidine residues are shown coordinating the iron (orange). The active site water (light blue) is shown in relation to the docked molecules. Molecules include (A) 9-cis-neoxanthin 2, (B) compound 17 and (C) compound 12. Sulfur heteroatoms in the two SLCCD compounds are highlighted in yellow.
Figure 12:
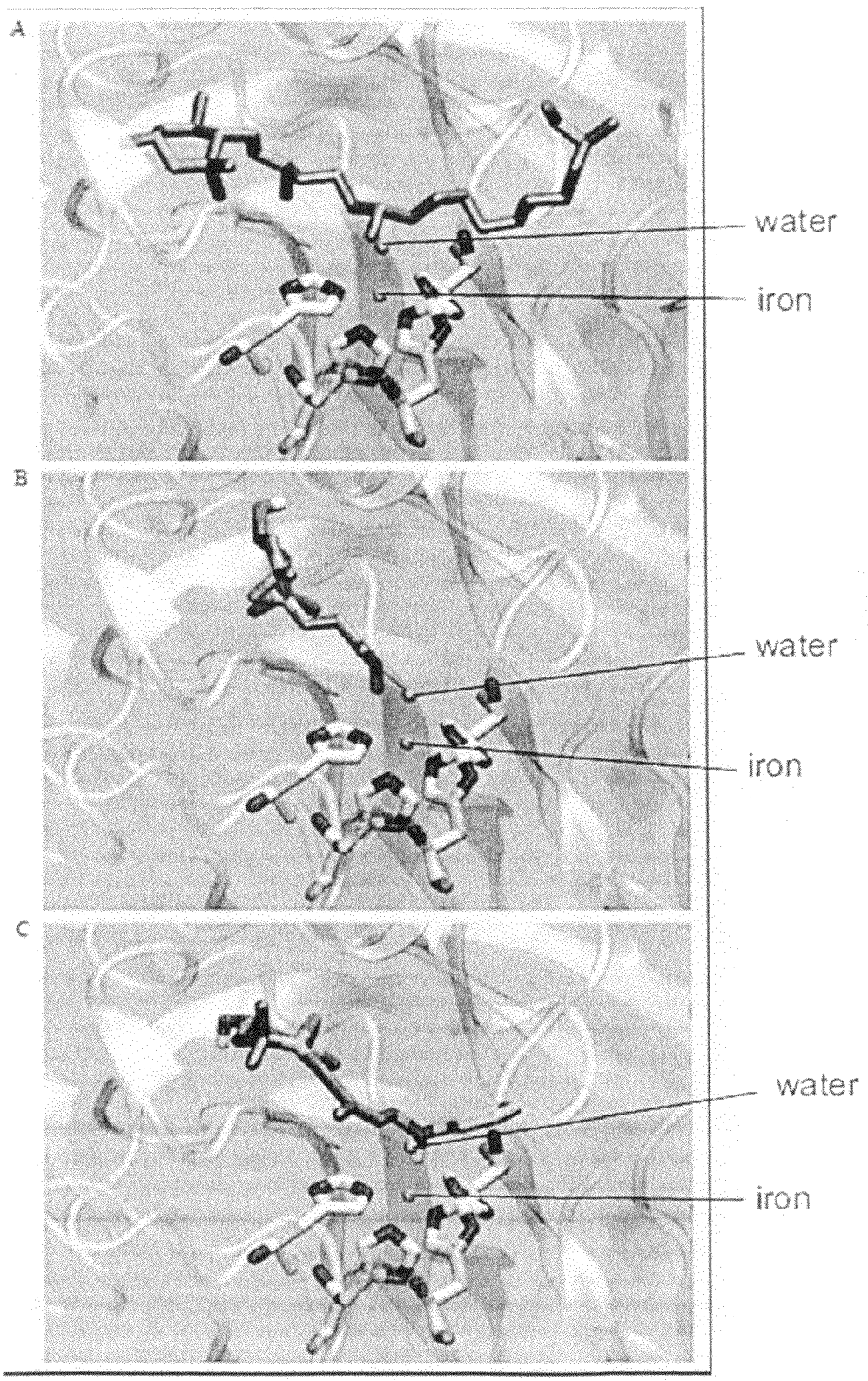
FIG. 12. Computational docking of compounds to the AtNCED3 homology model. Molecules include (A) 3-ON, (B) xanthoxin, (C) compound 18. Conserved histidine residues are shown coordinating the iron (orange). The active site water (light blue) is shown in relation to the docked molecules.

Recently a crystal structure was determined for *Synechocystis* apocarotenoid-15,15'-oxygenase (ACO), a fungal homologue of the NCEDs.[25] AtNCED3 shares 25% identity and 45% similarity with ACO at the amino acid level. Homology modeling using the Swiss-Model servers generated a hypothetical protein structure of AtNCED3 which maintained the octahedral coordination of the four active site histidines at 2.14, 2.05, 2.16 and 2.31 Å from the iron atom for H164, H211, H276 and H450 respectively.[26] Structural differences between the AtNCED3 model and ACO were limited to small surface exposed loops related to a few minor alignment gaps. As controls to test the AtNCED3 model, 9-cis-neoxanthin 2, the substrate of ACO (all-trans-(3R)-hydroxy-8'-apo-β-carotenol (3-ON)), and xanthoxin 4 structures were docked (FIGS. 6A, 12A and 12B). The 3-ON molecule docked to the AtNCED3 model with a similar orientation as observed in the ACO crystal with its β-ionone ring oriented towards the tunnel entrance but shifted in toward the catalytic site by 5 Å. This positions the C12 and C13 bond within 3.95 Å of the iron atom and 2.10 Å of a coordinated active site water molecule. Docking of 9-cis-neoxanthin 2 resulted in the epoxide ring entering the protein channel first, yielding a final orientation with the C11-C12 bond 4.4 Å away from and directly over the iron atom and 2.3 Å away from the active site water molecule. The xanthoxin molecule docked in the opposite orientation from the 9-cis-neoxanthin substrate, with its epoxide ring towards the tunnel entrance and its C10 carbon atom 3.6 Å and 1.9 Å from the iron atom and water molecule respectively.

Docking results correlated well with the in vitro enzyme assay data. Structures representing 12 (the more active stereoisomer of the racemic compound 13), 17 and 18 (FIGS. 6B, 6C and 12V, respectively) all docked in the same orientation as xanthoxin, in close proximity to the iron atom in the binding pocket. The nitrogen of 18 docked 2.67 Å away from the iron atom. The sulfur atoms of 12 and 17 docked 2.6 and 2.65 Å away from the iron atom respectively. Other SLCCD inhibitor molecules that performed poorly in the in vitro trials generally were not targeted to the catalytic site of the binding pocket, or in some instances were not targeted to the binding pocket at all during docking.

Effect of SLCCD Inhibitors on ABA Accumulation Under Osmotic Stress

*Arabidopsis thaliana* plants were treated with either ABM 9 or the inhibitor compounds 13, 17 and 18, to evaluate their ability to reduce ABA biosynthesis induced by an osmotic stress. Essentially plants were treated +/− inhibitor compound for 2 hours followed by mannitol stress-treatment in the presence of the same compounds. Mannitol stress has been shown to result in loss of turgor with a corresponding increase in ABA levels through the induction of AtNCED3 in *Arabidopsis thaliana*.[7,27]

Figure 7:
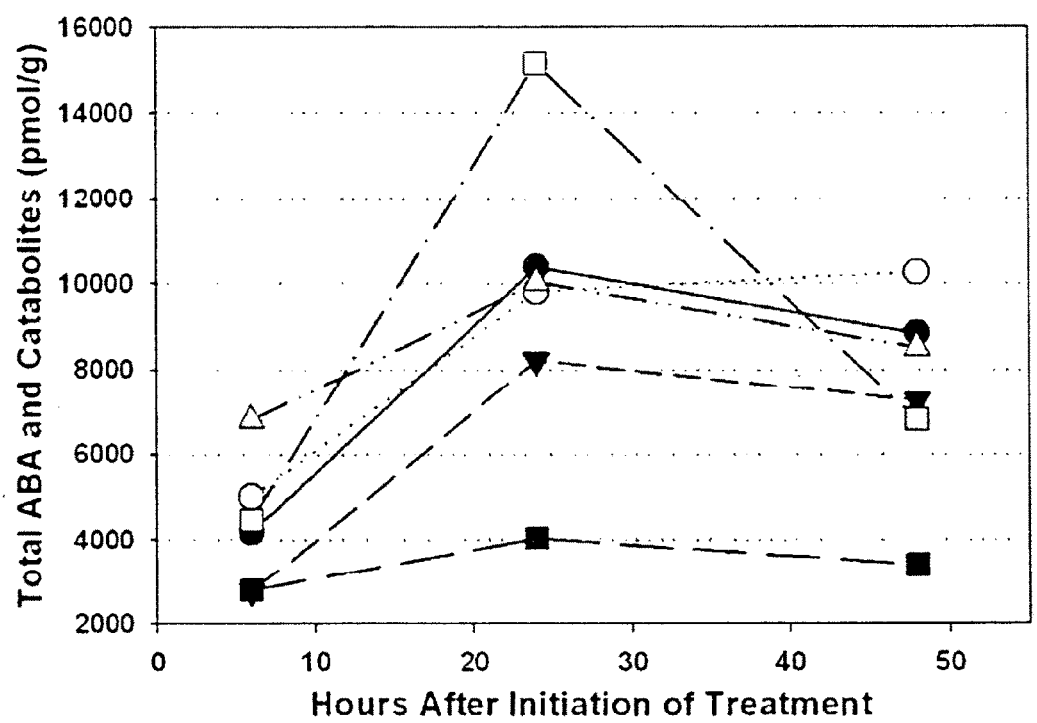
FIG. 7. Total ABA metabolite levels in mannitol stressed Arabidopsis thaliana plants treated with SLCCD inhibitors. Plants were treated with 33 µM inhibitors (compounds 13 (inverted closed triangles), 17 (closed circles), 18 (open circles) and ABM 9 (open triangles)) for 2 hours prior to being stressed with mannitol. Plants were harvested 6 hours after the inhibitor treatment and compared to plants that were mannitol stressed only (open squares), or non-treated/non-stressed plants (closed squares). Metabolites quantified and summed at each time point include abscisic acid-glucose ester, dihydrophaseic acid, phaseic acid and abscisic acid.
Figure 13:
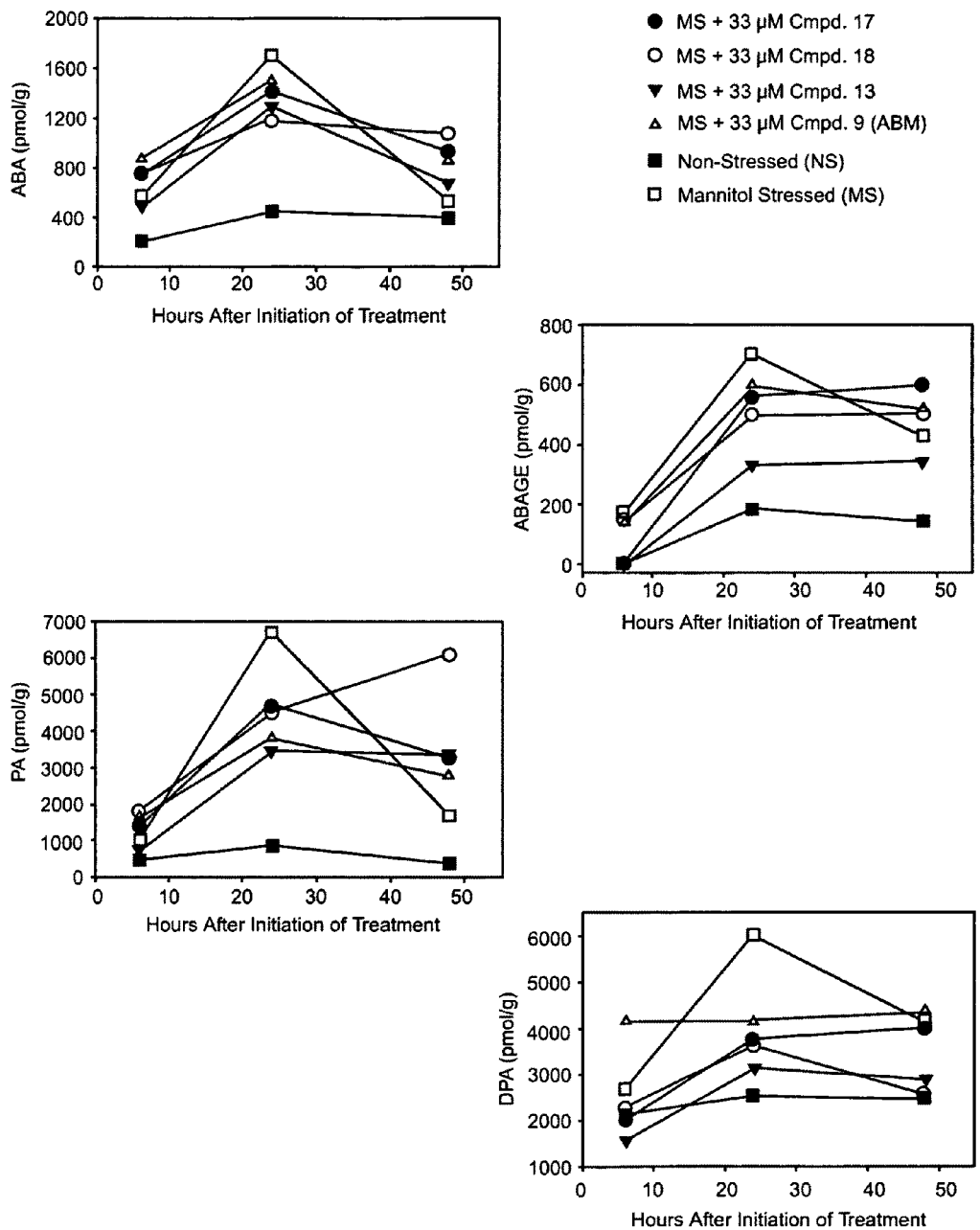
FIG. 13. Profiling of ABA and individual catabolites in plants treated with 33 µM of the indicated SLCCD compounds. Plants were treated with compounds for two hours prior to mannitol stress (MS) treatment. Time points (6, 24 and 48 hours) indicate samplings taken in hours following the initial compound treatment. Values are compared to those obtained from plants treated with mannitol only or non-treated/non-stressed plants. Metabolites quantified include abscisic acid (ABA, 1), abscisic acid-glucose ester (ABAGE, 8), dihydrophaseic acid (DPA, 7) and phaseic acid (PA, 6) as indicated in related plots.

As expected, mannitol treatment alone resulted in an elevation of the levels of ABA and catabolites peaking 24 hours after the imposition of treatment, compared to the levels in non-treated/non-stressed plants (FIG. 7). Accumulation of ABA and catabolites dropped off by 48 hours as described previously.[28] Treatment with compound 13 for two hours prior to and then during mannitol stress-treatment resulted in levels of ABA and catabolites remaining comparable to those of the non-treated/non-stressed control plants in the first 6 hours. By 24 hours, the total levels of ABA and catabolites in the compound 13 treated plants increased to only 8211 pmol/g, significantly below those of the mannitol-stressed only plants (15147 pmol/g). Similar treatment of plants with ABM 9 resulted in higher levels of ABA and catabolites at the first time point, with levels remaining constant (and higher than those for treatment with compound 13) over the remaining time course of the experiment. The remaining two inhibitors, 17 and 18, were less effective than 13 in reducing the effect of the osmotic stress on ABA and catabolite pools. Interestingly, the overall effect observed for compound 13 is not represented in individual plots of ABA levels (or any one other catabolite) alone (FIG. 13). It is only when total accumulation of ABA and its catabolites are considered that the overall effect becomes evident.

Effect of SLCCD Inhibitors on *Arabidopsis thaliana* Seed Germination

Figure 8:
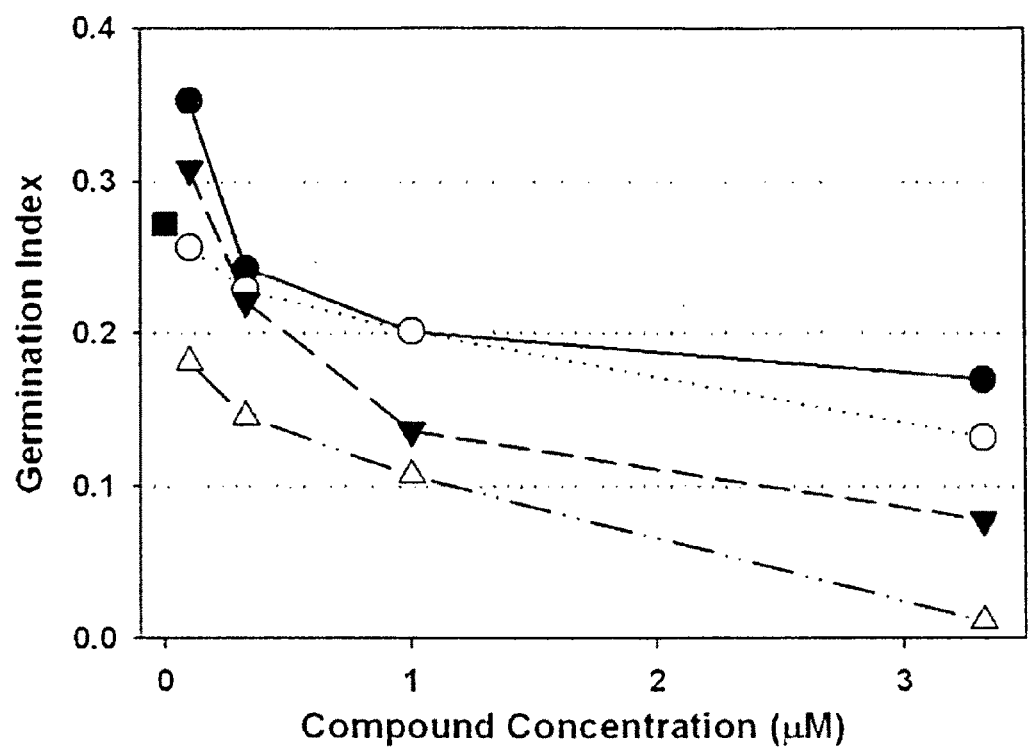
FIG. 8. Germination of Arabidopsis thaliana plants in the presence of each of SLCCD inhibitor compounds 18 (inverted closed triangles), 13 (closed circles), 17 (open circles), (+)-ABA 1 (open triangles), and germination of plants on media without added compounds (closed square).

Seed germination assays were performed for compounds 13, 17 and 18 to assess the ABA-like character of the inhibitors.[29] Inhibitors had relatively little effect on seed germination at low concentration compared to non-inhibitor treated and ABA treated controls (FIG. 8). At increasing concentrations (0.33 µM) the inhibitors did lead to reductions of seed germination by approximately 15%, compared to 47% for the (+)-ABA 1. Both compounds 13 and 17 reduced seed germination by 26% at 1 µM while 18 showed a more pronounced effect with a 50% reduction compared to 61% for (+)-ABA 1. At the highest concentration tested, compound 13 still only had a modest impact on seed germination at 38% reduction, while compounds 17 and 18 showed 51% and 71% reductions respectively, compared to 96% for (+)-ABA 1.

Figure 9A:
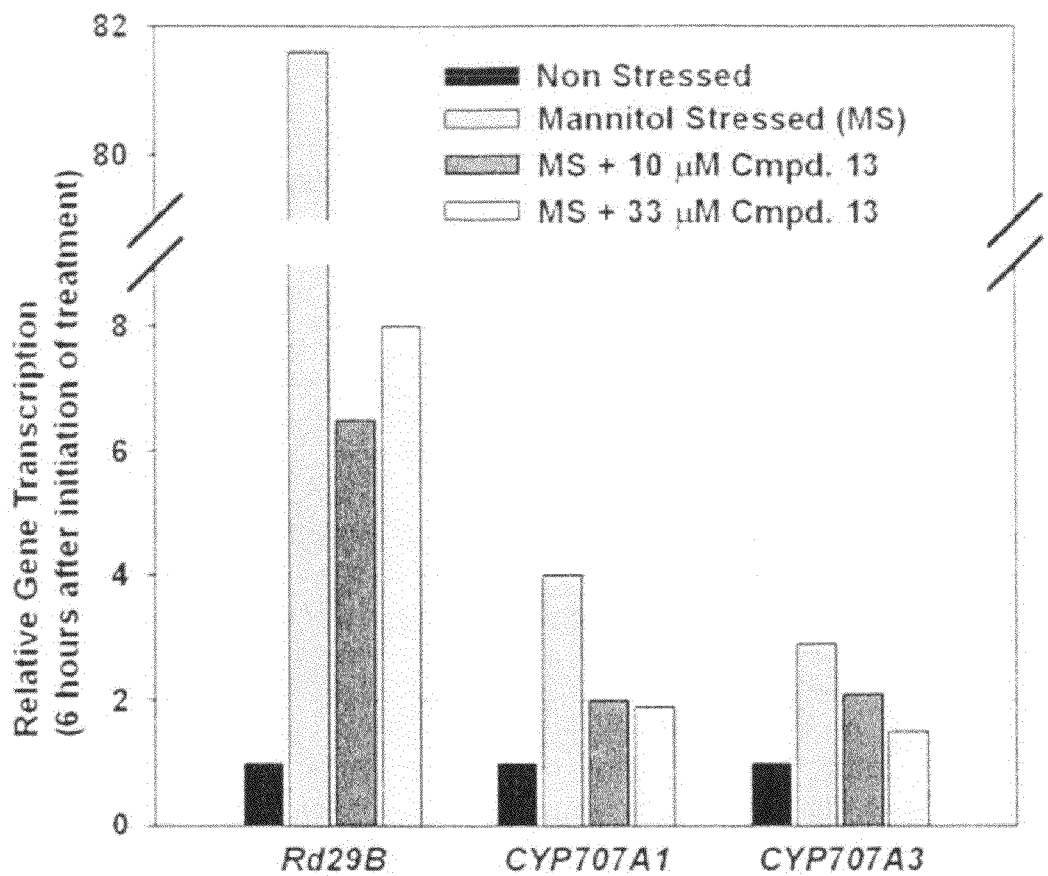
FIG. 9. Target gene transcript levels in mannitol stressed Arabidopsis thaliana plants treated with SLCCD inhibitors. A) Effect of compound 13. Plants were treated with 10 or 33 µM compound 13 for 2 hours prior to being stressed with mannitol. Plants were harvested 6 hours after the SLCCD compound treatment and compared to mannitol stressed only plants or non-treated/non-stressed plants. Target genes included Rd29B, CYP707A1 and CYP707A3. Transcript levels were normalized against the UBQ10 gene. B) Effects of SLCCD compounds on AtNCED3 expression. Experiments were carried out as described for A, but with each of SLCCD compounds 13, 17 and 18.
Figure 9B:
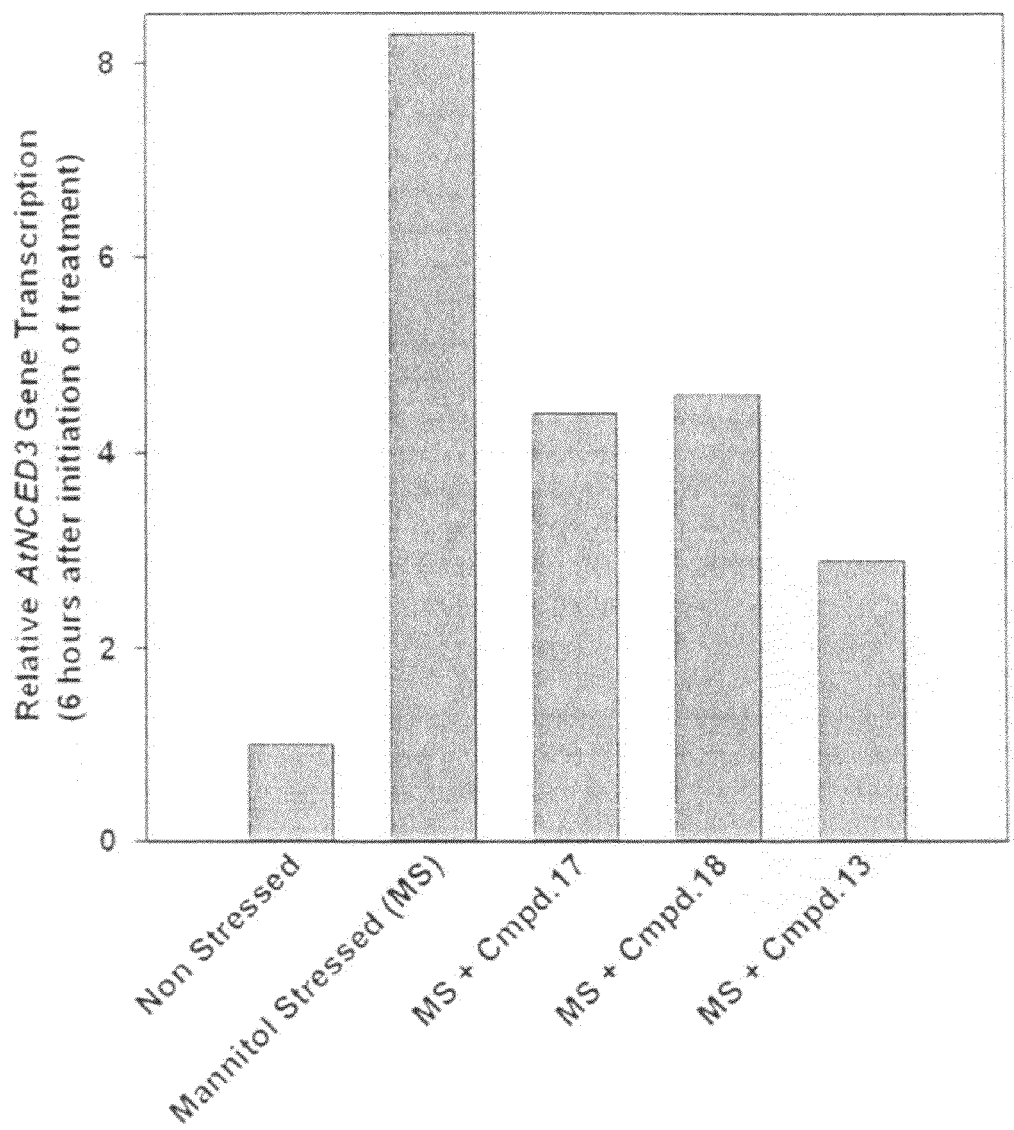
Figure 14:
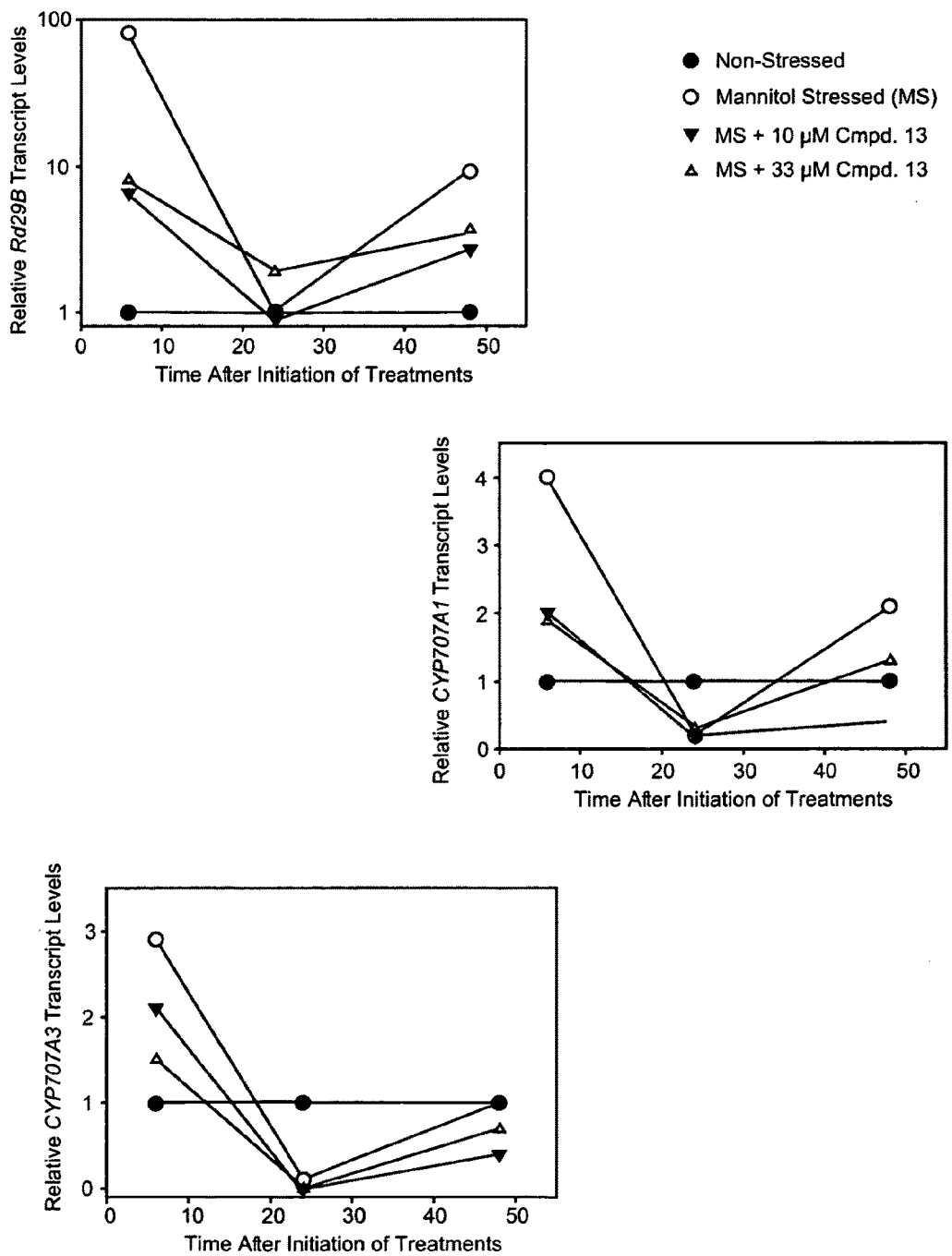
FIG. 14. Profiling of individual gene transcripts in plants treated with 10 or 33 µM compound 13 for two hours prior to mannitol stress (MS) treatment. Time points indicate samplings taken in hours following the initial compound treatment. Values are compared to those obtained from plants treated with mannitol only or non-treated/non-stressed plants. Quantified gene transcripts include, Rd29B, CYP707A1 and CYP707A3.
Figure 15:
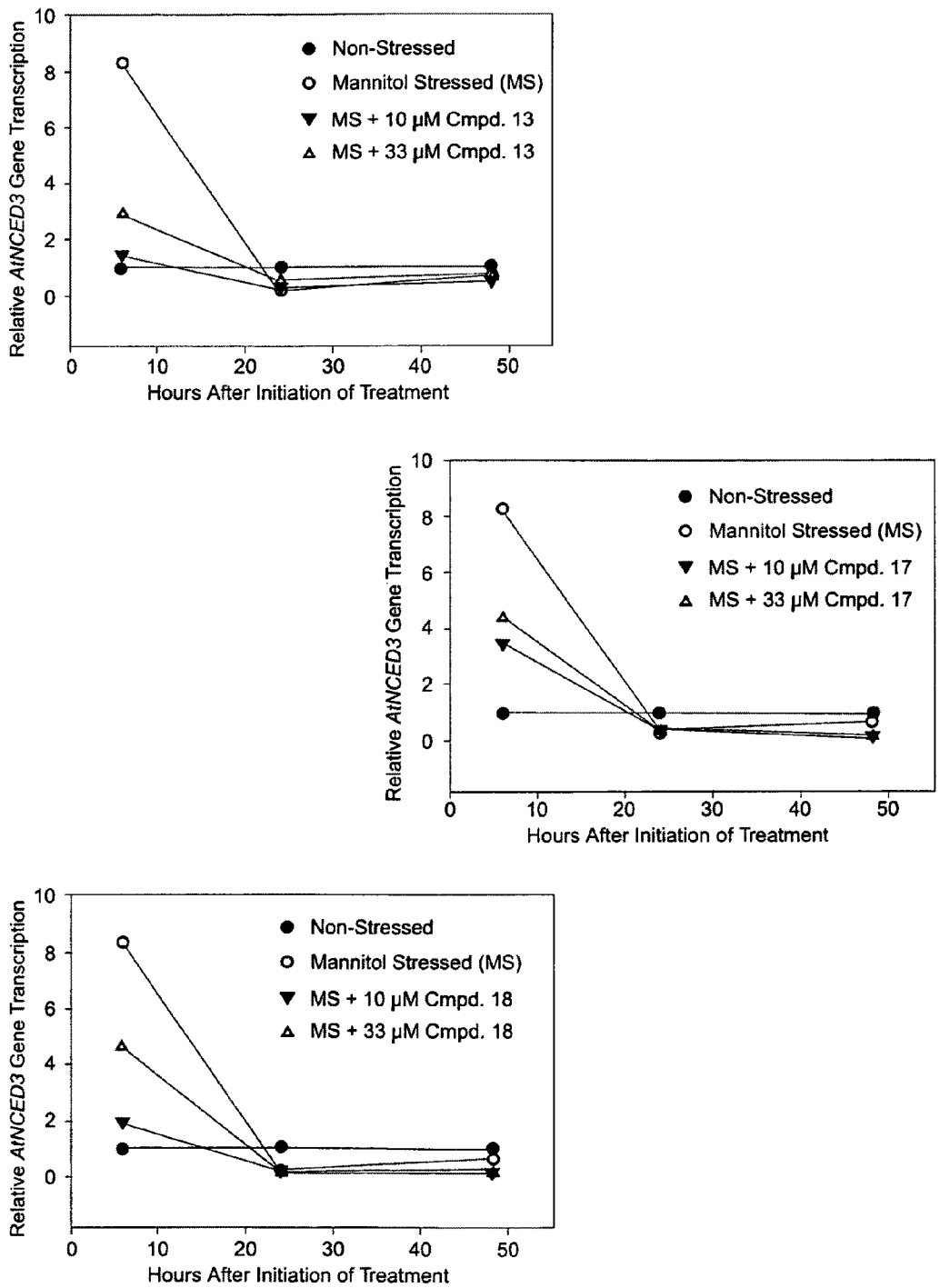
FIG. 15. Profiling of AtNCED3 gene transcription in plants treated with 10 and 33 µM of one of compounds 13, 17 or 18 for two hours prior to mannitol stress treatment (MS). Time points indicate samplings taken in hours following the initial compound treatment. Values are compared to those obtained from plants treated with mannitol only or non-treated/non-stressed plants.

Effect of SLCCD Inhibitors on Target Gene Transcript Levels Under Osmotic Stress In light of the observed effectiveness of compound 13 in moderating ABA and catabolite levels in vivo and its limited effect on seed germination, it was targeted for further evaluation. Specifically, quantitative reverse-transcription PCR was used to assess inhibitor induced changes in gene transcript levels in mannitol stressed plants. The gene targets chosen for this purpose were AtNCED3, the ABA and drought inducible Rd29B and the ABA (inducible) catabolic genes CYP707A1 and CYP707A3. Transcript levels were normalized against UBQ10 mRNA levels.[5,30,31] Mannitol treatment led to the induction of expression of all four target genes within 4 hours of the stress treatment (FIG. 9). Subsequently the mannitol-induced gene transcription levels decrease back to non-treated/non-stressed levels by 24 hours post-treatment and remained low through 48 hours (FIGS. 14 and 15). In general, pretreatment with compound 13 at both 10 and 33 µM concentrations prior to mannitol-stress led to reductions in the accumulation of mRNA transcript levels at 6 hours post-compound treatment for Rd29B, CYP707A1 and CYP707A3 compared to the mannitol-stressed control (FIG. 9A). The inhibition of mannitol-induced Rd29b transcription by compound 13 (about 90%) is especially striking and is consistent with the mannitol effect on Rd29b being primarily mediated by ABA. This result indicates the potential of this inhibitor for dissecting the role of ABA in physiological and developmental processes. As observed in mannitol stressed only plants, transcript levels in compound 13 pretreated plants decreased back to non-treated/non-stressed levels by 24 hours and remained low through 48 hours (FIG. 14). In addition to this, compound 13 was also found to decrease the relative expression levels of AtNCED3 in mannitol stressed plants (FIG. 9B). While the former results emphasize the lack of ABA-like character for compound 13, the moderation of AtNCED3 transcription represents a useful inhibitor-dependent side-effect that likely further contributes to lowering ABA levels in planta. Testing of compounds 17 and 18 demonstrated similar, although not as pronounced effects on AtNCED3 expression (FIG. 9B, FIG. 15).

Discussion:

Design/Synthesis and Inhibitory Activities of SLCCD Inhibitors

The design of inhibitors described herein focuses on specific interaction with the non-heme iron atom within AtNCED3, a definitive motif of carotenoid cleavage enzymes. It was envisioned that a molecule maintaining characteristics of the native enzyme substrate 9-cis-neoxanthin 2 or xanthoxin 4 product, but presenting a nitrogen or sulfur heteroatom might specifically occupy the active site of the enzyme with the heteroatom interacting with the non-heme iron, resulting in inactivation of the enzyme. Similar concepts have been applied to inhibitors of other dioxygenase enzymes.[32,33]

In earlier ABA structure activity studies, analogs with the side chain having a triple bond conjugated to a cis double bond were found to be highly active and were also readily synthesized.[20] Therefore the enyne feature was incorporated into the design of the present set of eight potential ABA biosynthesis inhibitors. The epoxy alcohol analogs 17 and 18, which most closely resemble the substrate and product of the NCED, strongly inhibited the NCED enzyme activity in vitro, and demonstrated higher inhibitory function than ABM 9 in this assay. However, in the experiment simulating drought stress, 17 and 18 were relatively weak inhibitors of ABA biosynthesis. As well, the aniline derivative 18 had a fairly pronounced (and undesirable) ABA-like effect on seed germination, with the thiophenyl analog 17 demonstrating a moderate effect.

Compounds with a tertiary alcohol at the junction of ring and side chain and either ketone or alcohol at C-4 were also envisioned to be possible inhibitors, as the general shape of the molecule and oxygen atom would be maintained. The keto allylic alcohol precursors 20, 21 and 22 were more conveniently prepared, affording both racemic and enantiomerically pure compounds. This was desirable as we had found earlier that the individual enantiomers 20 and 21 of the allylic alcohol 22 had different properties as competitive inhibitors of ABA perception.[34] The analog 20 competitively blocked ABA perception, while its enantiomer was a weak ABA agonist. On observing significant NCED inhibition with the racemic compound 13, comparable with that of ABM 9 and ABM-SG 10, we anticipated similar differences might be found in the present case, and the thioethyl derivatives of compounds 20 and 21 were synthesized and tested. Again, the stereochemistry of the analogs had an effect. Compound 12 inhibited the enzyme as strongly as the more xanthoxin-like compounds, while the other enantiomer 11 had reduced activity in the in vitro enzyme assay. Two diasteromeric hydroxy compounds 14 and 15 were synthesized to explore the effect of changing the oxidation level of the C-4 or position of the oxygen atom. In the in vitro enzyme assay, the hydroxyl compounds did not afford greater activity. Compound 16 was incorporated into the set of test molecules to determine if positioning the sulfur atom further from the cyclohexanone ring would have an effect on activity compared to that of 13.

Computational Analysis of SLCCD Inhibitor-Enzyme Complexes

In the ACO structure the binding pocket entrance is proposed to act as a bottleneck, arresting movement of 3-ON to the interior and positioning the C15-C15' bond over the iron molecule in a trans conformation.[25] In contrast, AtNCED3 must accept substrate molecules with rings at both extremities, and thus it would be expected that the binding pocket entrance be sufficiently large to allow ring structures to enter the cavity. Therefore in contrast to ACO, AtNCED3 likely determines substrate positioning based on where the molecule interacts with the internal terminus of the binding pocket. Docking to the AtNCED3 model highlights that this is likely the case, as 3-ON was oriented with its C13-C14 bond over the iron, and the β-ionone ring pulled inside the tunnel entrance. Docking of 9-cis-neoxanthin 2 resulted in the epoxide ring being buried in the AtNCED3 catalytic pocket. This positioned the C11-C12 bond over the iron atom in a suitable position for catalytic cleavage at the expected location. These results emphasize the validity and potential utility of the AtNCED3 model.

The xanthoxin 4 molecule docked with its epoxide ring in the opposite orientation (similar to 3-ON) to that of the 9-cis-neoxanthin 2. While this likely does not represent its native orientation following cleavage of the 9-cis-neoxanthin 2 substrate, it emphasizes the accommodating size of the AtNCED3 entrance tunnel and that the preferred orientation of single ring containing molecules is with the ring pointing toward the entrance. Docking results for the SLCCD inhibitors seem to follow this preference with the hydroxylated rings preferentially pointing toward the entrance.

In the ACO crystal structure a coordinated water molecule occupies the fifth ligand position within the iron octahedral co-ordination structure. The water molecule, theorized to be an oxygen donor and required for catalytic activity, is located 3.2 Å from the C15 of the substrate and 2.07 Å from the non-heme iron atom.[25] Each of the three active SLCCD inhibitors docked with their heteroatoms (nitrogen or sulfur) within 2.7 Å of the iron atom such that they would be sufficient to occupy the coordinate space of the water molecule in the ACO structure and stop catalysis.

In Vivo Effects of SLCCD Inhibitors

The basic premise of this work lies in the design of inhibitors that bind to and inactivate the NCED enzyme responsible for the first committed step in ABA 1 biosynthesis. In a recent study on effects of drought stress on signaling and gene expression in *Arabidopsis*, it had been shown that the levels of ABA and its catabolites phaseic acid 6, dihydrophaseic acid 7 and ABA glucose ester 8 were all found to increase on imposition of the stress.[28] In the present study to compare the effects of potential inhibitors on ABA biosynthesis capacity, an osmotic stress treatment of *Arabidopsis* plants was substituted for the drought stress. ABA biosynthetic inhibitors were designed and tested and in the case of compound 13 were shown to significantly reduce the accumulation of ABA 1 and the catabolites 6, 7, and 8 in plants subjected to osmotic stress. While the rationale for inhibitor design was based on maintaining structural characteristics similar to the enzymes substrate and products to maximize specificity, this also meant that the inhibitors share structural characteristics with ABA 1 itself. Obviously an inhibitor of ABA 1 biosynthesis should not mediate ABA signaling.

Toward assessing the ABA-like character of the inhibitors their ability to mediate known ABA 1 effects at the levels of seed germination and gene regulation were determined. In general, the SLCCD inhibitors were found to be weaker germination inhibitors than (+)-ABA 1, with compound 13 having 60-70% less effect. Interestingly, low concentrations of compounds 13 and 17 had slight promotion effects on seed germination. As well, treatment of mannitol-stressed plants with compound 13 led to a reduction of transcript levels for three genes known to be (+)-ABA 1 inducible.[5,30] The reduction of transcription mediated by this inhibitor is in agreement with previous observations made for alternate inhibitors and likely results from the reduction of endogenous ABA 1 levels.[17] Overall, these results emphasize that SLCCD inhibitor 13 does not generally simulate ABA-inducible responses and thus does not maintain ABA-like characteristics.

Finally, these pilot in vivo studies demonstrate that mannitol stress leads to induction of AtNCED3 gene expression as reported previously.[7] While stress induced, it is not clear whether AtNCED3 is specifically ABA-inducible. But from the results reported here, it is clear that application of the SLCCD inhibitors significantly reduces AtNCED3 mRNA levels under stress conditions, which would further contribute to reducing ABA 1 biosynthesis in planta. While this characteristic was not specifically sought in designing the inhibitors, in terms of the overall objective of inhibiting ABA 1 biosynthesis, a reduction in the primary biosynthetic enzyme is a very useful side effect The relatively lesser effects of inhibitors 17 and 18 in planta were surprising considering their effectiveness in vitro and docking results in silico. This lowering of efficacy in moderating ABA levels in vivo could be due to many factors, including stability of the different compounds in the plant and the presence of the hydrophobic aromatic rings in both 17 and 18 structures, possibly reducing their permeability through the roots and transport to the site of action. The discrepancy between in vitro and in vivo results is consistent also in the AtNCED3 expression profiling where 13 led to the highest reduction of stress-induced gene expression.

Synthesis of ABA Analogue Inhibitors

EXAMPLE 1

(4S,5R)-(3'Z)-4-(5'-(Ethylthio)-3'-methylpent-3'-en-1'-ynyl)-4-hydroxy-3,3,5-trimethylcyclohexanone (11)

A solution of alcohol 20[20] (25 mg, 0.1 mmol), ethyl disulfide (25 μL, 0.2 mmol) and n-Bu$_3$P (49 μL, 0.2 mmol) in CH$_2$Cl$_2$ (1.5 mL) was stirred at room temperature for 4.5 h. Ethanol (1 mL) was added to the reaction and the resulting mixture was stirred for 20 min. Ethanol was removed by evaporation and CH$_2$Cl$_2$ (15 mL) was added. The organic phase was washed with 0.5 N NaOH and brine successively, dried and concentrated to give a residue which was purified by FCC (ethyl acetate/hexane, 15:85 v/v) to provide 11 (19.2 mg, 62%) and recover 20 (4 mg, 19%).

$[\alpha]^{25}_D$-16 (c 0.48, CHCl$_3$); IR (KBr): 3463, 2975, 2872, 1688 cm$^{-1}$; $^1$H NMR (CDCl$_3$) δ: 5.76 (1H, dt, 1.25, 7.75 Hz, =CH), 3.31 (2H, d, 8.75 Hz, CH$_2$S), 2.65 (1H, d, 14.25 Hz, H-2), 2.48 (2H, q, 7.5 Hz, SCH$_2$CH$_3$), 2.29 (3H, m, H-5 & H-6), 2.08 (1H, d, 14.25 Hz, H-2), 1.89 (3H, s, CH$_3$), 1.22 (3H, t, 7.5 Hz, SCH$_2$CH$_3$), 1.20 (3H, s, CH$_3$), 1.14 (3H, s, CH$_3$), 0.97 (3H, s, CH$_3$); $^{13}$C NMR (CDCl$_3$) δ: 209.2, 134.2, 119.5, 92.6, 86.8, 77.4, 52.9, 47.0, 42.2, 37.4, 31.6, 25.9, 25.4, 23.2, 20.8, 16.6, 14.9; HRMS EI$^+$ m/z calc. for C$_{17}$H$_{26}$O$_2$S: 294.1654. found: 294.1655.

EXAMPLE 2

(4R,5S)-(3'Z)-4-(5'-(Ethylthio)-3'-methylpent-3'-en-1'-ynyl)-4-hydroxy-3,3,5-trimethylcyclohexanone (12)

A solution of alcohol 21[20] (28 mg, 0.11 mmol), diethyl sulfide (28 μL, 0.22 mmol) and n-Bu$_3$P (55 μL, 0.22 mmol) in CH$_2$Cl$_2$ (2 mL) was stirred at room temperature for 6 h. Work up as described above, followed by purification by FCC (ethyl acetate/hexane, 15:85 v/v) to afford 12 (22 mg, 63%).

[α]$^{25}_D$ +15 (c 1.0, CHCl$_3$). The spectral characterization data was identical to enantiomer 11.

EXAMPLE 3

(4S,5R/4R,5S)-(3'Z)-4-(5'-(Ethylthio)-3'-methylpent-3'-en-1'-ynyl)-4-hydroxy-3,3,5-trimethylcyclohexanone (13)

A solution of allylic alcohol 22, protected as the neopentylglycol ketal[20], (34 mg, 0.1 mmol), ethyl disulfide (34 µL, 0.27 mmol) and n-Bu$_3$P (62 µL, 0.25 mmol) in CH$_2$Cl$_2$ was stirred at room temperature for 4.5 h. Work up as described above, followed by purification by FCC (ethyl acetate/hexane, 10:90 v/v) to afford the sulfide (22.1 mg, 58%).

$^1$H NMR (CDCl$_3$) δ: 5.67 (1H, ddq, 1.5, 7.75, 7.75 Hz, =CH), 3.54 (2H, d, 11.25 Hz, OCH$_2$), 3.36 (2H, ddd, 1.75, 11.25, 13.25 Hz, OCH$_2$), 3.31 (2H, dd, 0.75, 7.75 Hz, SCH$_2$), 2.48 (2H, q, 7.5 Hz, SCH$_2$CH$_3$), 2.24 (1H, dd, 3.25, 14.25 Hz, H-2), 2.18 (1H, m, H-5), 1.96 (1H, dt, 3.25, 13.5, H-6), 1.87 (3H, d, 1.0 Hz, CH$_3$), 1.57 (1H, dd, 13.5, 13.5 Hz, H-6), 1.46 (1H, d, 14.25 Hz, H-2), 1.22 (3H, t, 7.5 Hz, CH$_3$), 1.12 (3H, s, CH$_3$), 1.09 (3H, s, CH$_3$), 1.04 (3H, d, 7.5 Hz, CH$_3$), 1.04 (3H, s, CH$_3$), 0.82 (3H, s, CH$_3$).

To a solution of the ketal protected sulfide (160 mg, 0.4 mmol) in acetone (5 mL) was added 2N HCl (8 drops). The mixture was stirred at room temperature for 40 min. After evaporation of acetone, ether was added and washed with sat. NaHCO$_3$, dried and concentrated to give a residue which was purified by FCC (ethyl acetate/hexane 20:80 v/v) to provide 13 (100 mg, 80%). The spectral characterization data was identical to pure enantiomer 11.

EXAMPLE 4

(1S,4R,6R)-(3'Z)-1-(5'-(Ethylthio)-3'-methylpent-3'-en-1'-ynyl)-2,2,6-trimethylcyclohexane-1,4-diol (14)

A solution of allylic alcohols 23 and 24[20] (200 mg, 0.55 mmol), (C$_2$H$_5$S)$_2$ (102 µL, 0.83 mmol) and n-Bu$_3$P (203 µL, 0.83 mmol) in CH$_2$Cl$_2$ (5 mL) was stirred at room temperature for 6 h. Work up as described above, followed by purification by FCC (ethyl acetate/hexane, 5:95 v/v) to provide 25 (41 mg, 17%), 26 (18.4 mg, 8%) and recovery of the unreacted starting material (70 mg, 35%).

For 25: $^1$H NMR (CDCl$_3$) δ: 5.67 (1H, dt, 1.5, 7.75 Hz, =CH), 3.92 (1H, m, H-4), 3.32 (2H, dd, 0.75, 7.75 Hz, CH$_2$S), 2.49 (2H, q, 7.25 Hz, SCH$_2$CH$_3$), 2.32 (1H, m, H-6), 1.87 (3H, d, 1.0 Hz, CH$_3$), 1.76 (1H, br s, OH), 1.62 (1H, dd, 3.5, 14.25 Hz, H-3), 1.57 (2H, m, H-5), 1.49 (1H, d, 14.25 Hz, H-3), 1.23 (3H, t, 7.25 Hz, SCH$_2$CH$_3$), 1.20 (3H, s, CH$_3$), 1.06 (3H, s, CH$_3$), 1.04 (3H, d, 6.5 Hz, CH$_3$), 0.86 (9H, s, SiCMe$_3$), 0 (6H, s, SiMe$_2$).

To a solution of 25 (41 mg, 0.1 mmol) in THF (1.5 mL) was added TBAF (1 M solution in THF, 0.5 mL, 0.5 mmol). The reaction mixture was stirred at room temperature for 1 day and diluted with ether. The mixture was washed with water (10 mL×3), dried, concentrated and fractionated by FCC (10% ethyl acetate/hexane, 10:90 v/v increased to 35:65 v/v) to provide 14 (21.3 mg, 71%).

[α]$^{25}_D$ −13 (c 0.94, CH$_2$Cl$_2$); IR (KBr): 3332, 2976, 2879, 1450 cm$^{-1}$; $^1$H NMR (CDCl$_3$) δ: 5.67 (1H, dt, 1.5, 7.75 Hz, =CH), 4.0 (1H, m, H-4), 3.30 (2H, dd, 1.0, 7.75 Hz, CH$_2$S), 2.47 (2H, q, 7.5 Hz, SC$_2$H$_5$), 2.32 (1H, m, H-6), 1.85 (3H, s, CH$_3$), 1.63 (4H, m, H-5 & H-3), 1.19 (3H, t, 7.5 Hz, SC$_2$H$_5$), 1.19, (3H, s, CH$_3$), 1.08 (3H, s, CH$_3$), 1.03 (3H, d, 6.5 Hz, CH$_3$); $^{13}$C NMR (CDCl$_3$) δ: 133.2, 120.0, 94.1, 85.7, 79.1, 66.8, 44.5, 40.1, 38.8, 31.9, 31.6, 27.5, 25.2, 23.3, 23.1, 16.1, 14.9; HRMS Cl$^+$ NH$_3$ m/z calc. for C$_{17}$H$_{32}$NO$_2$S: 314.2154. found: 314.2162.

EXAMPLE 5

(1R,4R,6R)-(3'Z)-1-(5'-(Ethylthio)-3'-methylpent-3'-en-1'-ynyl)-2,2,6-trimethylcyclohexane-1,4-diol (15)

To a solution of 26[20] (18.4 mg, 0.045 mmol) in THF (1.2 mL) was added TBAF (1.0 M solution in THF, 0.13 mL, 0.13 mmol). The reaction was stirred at room temperature for 1 day. Work up as for 14 to provide product 15 (8.5 mg, 64%) and recovered starting material (4.5 mg, 24%).

[α]$^{25}_D$ +10 (c 0.25, CH$_2$Cl$_2$); IR (KBr): 3388, 2968, 2922, 1458 cm$^{-1}$; $^1$H NMR (CDCl$_3$) δ: 5.71 (1H, dt, 1.5, 7.75 Hz, =CH), 3.87 (1H, m, H-4), 3.33 (2H, dd, 1.0, 7.75 Hz, CH$_2$S), 2.51 (2H, q, 7.7 Hz, SC$_2$H$_5$), 2.00 (1H, m, H-6), 1.88 (3H, d, 1.5 Hz, CH$_3$), 1.67 (1H, ddd, 2.5, 4.5, 12.75 Hz, H-5), 1.57 (1H, dd, 11.5, 12.5 Hz, H-5), 1.35 (1H, dd, 12.5, 24.25 Hz, H-3), 1.23 (3H, t, 7.25 Hz, CH$_3$), 1.13 (3H, s, CH$_3$), 1.07 (3H, d, 6.5 Hz, CH$_3$), 1.02 (3H, s, CH$_3$); $^{13}$C NMR (CDCl$_3$) δ: 133.4, 119.9, 93.9, 86.3, 78.3, 66.2, 46.8, 41.7, 39.9, 35.7, 31.6, 27.0, 25.3, 23.2, 20.8, 16.5, 14.9; HRMS EI$^+$ m/z calc. for C$_{17}$H$_{25}$O$_2$S: 296.1810. found: 296.1822.

EXAMPLE 6

(1R,3S,6R)-(3'Z)-6-(5'-Hydroxy-3'-methylpent-3'-en-1'-ynyl)-1,5,5-trimethyl-7-oxa-bicyclo[4.1.0]heptan-3-ol (28)

A mixture of compound 27[20] (18 mg, 0.1 mmol), (Z)-3-iodobut-2-en-1-ol (30 mg, 0.15 mmol), CuI (15 mg, 0.08 mmol) and (Ph$_3$P)$_4$Pd (23 mg, 0.02 mmol) in (i-Pr)$_2$NH (0.3 mL) was stirred at room temperature for 17 h. Saturated NH$_4$Cl solution was added to quench the reaction. The mixture was extracted with ether, dried, concentrated and fractioned by FCC (ethyl acetate/hexane, 60:40 v/v) to provide compound 28 (18.1 mg, 72%).

[α]$^{25}_D$ −8.0 (c 1.2, CHCl$_3$); IR (KBr): 3333, 2959, 2923 cm$^{-1}$; $^1$H NMR (CDCl$_3$) δ: 5.85 (1H, ddq, 1.0, 6.75, 6.75 Hz, =CH), 4.26 (2H, d, 6.75 Hz, =CHCH$_2$), 3.79 (1H, m, H-3), 2.32 (1H, ddd, 1.75, 5, 14.25 Hz, H-2), 1.84 (3H, d, 1 Hz, CH$_3$), 1.74 (1H, br s, OH), 1.61 (1H, dd, 8.75, 14.25 Hz, H-2), 1.57 (1H, m, H-4), 1.47 (3H, s, CH$_3$), 1.22 (3H, s, CH$_3$), 1.19 (1H, dd, 10.5, 13.0 Hz, H-2), 1.08 (3H, s, CH$_3$); $^{13}$C NMR (C$_6$D$_6$) δ: 137.8, 119.1, 92.4, 84.3, 66.6, 63.8, 63.6, 61.5, 45.7, 40.0, 34.4, 30.0, 26.2, 22.9, 22.0; HRMS Cl$^+$ m/z calc. for C$_{15}$H$_{23}$O$_3$: 251.1647. found: 251.1646.

EXAMPLE 7

(1R,3S,6R)-(3'Z)-1,5,5-Trimethyl-6-(3'-methyl-5'-(phenylthio)-pent-3'-en-1'-ynyl)-7-oxa-bicyclo[4.1.0]heptan-3-ol (17)

A solution of alcohol 28 (56.6 mg, 0.23 mmol), phenyl disulfide (98.9 mg, 0.45 mmol) and n-Bu$_3$P (112 µL, 0.45 mmol) in dry CH$_2$Cl$_2$ (3 mL) was stirred at room temperature for 3 h. Ethanol (1 mL) was added to the reaction and stirred for 30 min. Ethanol was evaporated off and more CH$_2$Cl$_2$ added. The organic phase was washed with 0.5 N NaOH, followed by water and then dried, concentrated, and fractionated by FCC (ethyl acetate/hexane, 30:70 v/v) to give product 17 (42 mg, 54%).

$[\alpha]^{25}_D$ −16 (c 0.84, CHCl$_3$); IR (KBr): 3438, 2961, 2924, 1583 cm$^{-1}$; $^1$H NMR (CDCl$_3$) δ: 7.31 (2H, m, C$_6$H$_5$), 7.23 (2H, m, C$_6$H$_5$), 7.14 (1H, m, C$_6$H$_5$), 5.73 (1H, ddq, 1.0, 7.5, 7.5 Hz, =CH), 3.82 (1H, m, H-3), 3.71 (2H, dd, 0.75, 7.5 Hz, CH$_2$S), 2.34 (1H, ddd, 1.75, 5.0, 14.5 Hz, H-2), 1.81 (3H, d, 1.0 Hz, CH$_3$), 1.63 (1H, dd, 8.5, 14.5 Hz, H-2), 1.58 (1H, m, H-4), 1.47 (3H, s, CH$_3$), 1.23 (3H, s, CH$_3$), 1.21 (1H, m, H-4), 1.10 (3H, s, CH$_3$); $^{13}$C NMR (CDCl$_3$) δ: 135.9, 132.9, 129.3, 128.9, 126.0, 120.7, 91.7, 84.2, 67.1, 63.8, 63.7, 45.8, 39.8, 34.4, 33.9, 29.9, 25.7, 22.9, 21.7; HRMS EI$^+$ m/z calc. for C$_{21}$H$_{26}$O$_2$S: 342.1654. found: 342.1659.

EXAMPLE 8

(1'R,4S,6'R)-(2Z)-5-(4'-Hydroxy-2',2',6'-trimethyl-7-oxa-bicyclo[4.1.0]heptan-1'-yl)-3-methylpent-2-en-4-ynal (29)

A mixture of alcohol 28 (89 mg, 0.36 mmol) and MnO$_2$ (774 mg, 8.9 mmol) in petroleum ether (10 mL) and ethyl acetate (5 mL) was stirred at room temperature for 4 h. The reaction mixture was filtered through a pad of Celite 545™ and washed with ethyl acetate. The combined filtrates and washings were concentrated and purified by FCC (ethyl acetate/hexane, 30:70 v/v) to afford aldehyde 29 (73.3 mg, 83%).

$[\alpha]^{25}_D$ −11 (c 3.0, CHCl$_3$); IR (KBr): 3456, 2918, 1601, 1593 cm$^{-1}$; $^1$H NMR (C$_6$D$_6$) δ: 10.27 (1H, d, 8.0 Hz, CHO), 5.88 1H, dd, 0.75, 8.0 Hz, =CH), 3.55 (1H, m, H-4), 2.03 (1H, ddd, 1.0, 5.0, 15.5 Hz, H-5), 1.46 (3H, d, 0.75 Hz CH$_3$), 1.36 (2H, m, H-3 and H-5), 1.27 (3H, s, CH$_3$), 1.13 (3H, s, CH$_3$), 1.11 (3H, s, CH$_3$), 0.99 (1H, dd, 10.0, 13.0 Hz, H-3); $^{13}$C NMR (C$_6$D$_6$) δ: 190.8, 140.1, 136.3, 98.4, 82.5, 67.0, 63.4, 45.4, 39.8, 34.3, 29.6, 26.1, 24.1, 21.8; HRMS Cl$^+$ m/z calc. for C$_{15}$H$_{21}$O$_3$: 249.1491. found: 249.1489. 5.1.9.

(1R,3S,6R)-(3'Z)-1,5,5-Trimethyl-6-(3'-methyl-5'-(phenylamino)-pent-3'-en-1-ynyl)-7-oxabicyclo[4.1.0]heptan-3-ol (18)

A solution of aldehyde 29 (16 mg, 0.065 mmol) and aniline (10 µL, 0.11 mmol) in ethanol (1.5 mL) was refluxed for 30 min. The reaction mixture was cooled to room temperature and then NaBH$_4$ (7.4 mg, 0.2 mmol) was added. The resulting mixture was stirred at room temperature for 15 min. and water (3 mL) with glacial acetic acid (1 drop) was added. The ethanol was evaporated off and water phase was extracted with ether, dried, concentrated and fractionated by FCC (ethyl acetate/hexane, 35:65 v/v) to provide product 18 (17 mg, 81%).

$[\alpha]^{25}_D$ −13 (c 1.4, CHCl$_3$); IR (KBr): 3410, 2960, 1602, 1504 cm$^{-1}$; $^1$H NMR (C$_6$D$_6$) δ: 7.15 (2H, m, C$_6$H$_5$), 6.73 (1H, dd, 7.25, 7.25 Hz, C$_6$H$_5$), 6.52 (2H, dd, 1.0, 8.5 Hz, C$_6$H$_5$), 5.47 (1H, ddq, 1.5, 6.5, 6.5 Hz, =CH), 3.80 (2H, m, CH$_2$NH), 3.62 (1H, m, H-3), 2.09 (1H, ddd, 1.5, 5.0, 14.5 Hz, H-2), 1.67 (3H, d, 1.25, CH$_3$), 1.44 (3H, s, CH$_3$), 1.40 (2H, m, H-2 & H-4), 1.31 (3H, s, CH$_3$), 1.23 (3H, s, CH$_3$), 1.05 (1H, dd, 9.75, 13.0 Hz, H-4); $^{13}$C NMR (C$_6$D$_6$) δ: 148.4, 136.5 129.5, 119.8, 117.7, 113.2, 92.9, 84.5, 66.6, 63.6, 45.7, 44.1, 40.0, 34.4, 30.1, 26.2, 22.9, 22.0; HRMS TOF$^+$ m/z calc. for C$_{21}$H$_{28}$NO$_2$: 326.2114. found: 326.2123.

EXAMPLE 9

(2Z,4E)-5-(1'-Hydroxy-2',2',6'-trimethyl-4'-oxocyclohexyl)-3-methylpenta-2,4-dienyl 2-(thiophen-2''-yl)acetate (16)

To a solution of the allylic alcohol, racemic 20 from reference[20], (34 mg, 0.1 mmol), Et$_3$N (42 µL, 0.3 mmol) in CH$_2$Cl$_2$ (1.5 mL) was added 2-thiopheneacetyl chloride (18 µL, 0.15 mmol). The reaction mixture was stirred at room temperature for 4 h and diluted with CH$_2$Cl$_2$. The organic phase was washed with saturated NaHCO$_3$, dried, concentrated and fractionated by PTLC (ethyl acetate/hexane, 20:80 v/v) to the ketal protected thiophene ester (13 mg, 28%).

$^1$H NMR (CDCl$_3$): 7.19 (1H, d, 1.25 Hz, SCH), 6.93 (2H, m, thiophene CH=CH), 6.67 (1H, d, 15.5 Hz, CH=CH), 5.98 (1H, d, 15.5 Hz, CH=CH), 5.47 (1H, t, 7.0 Hz, =CHCH$_2$O), 4.80 (2H, d, 7.0 Hz, CH$_2$O), 3.82 (2H, s, COCH$_2$), 3.58 (2H, dd, 5, 10.25 Hz, OCH$_2$), 3.41 (2H, dd, 5, 10.25 Hz, OCH$_2$), 2.30 (1H, dd, 2.75, 14.5 Hz, H-3), 2.17 (1H, m, H-6'), 1.98 (1H, dd, 3.25, 14.25 Hz, H-5'), 1.86 (3H, s, CH$_3$), 1.40 (1H, d, 14.0 Hz, H-3'), 1.35 (1H, d, 14.0 Hz, H-3'), 1.12 (3H, s, CH$_3$), 1.06 (3H, s, CH$_3$), 0.85 (3H, s, CH$_3$), 0.78 (3H, s, CH$_3$), 0.77 (3H, d, 8.0 Hz, CH$_3$).

To a solution of the ketal protected thiophene ester (13 mg, 0.028 mmol) in acetone (1.5 mL) was added 2N HCl (2 drops). The mixture was stirred at room temp. for 1 h. After removing acetone, ether was added and washed with saturated NaHCO$_3$, dried and concentrated to give a residue which was purified by FCC (ethyl acetate/hexane, 20:80 v/v) to provide 16 (8 mg, 75%).

IR (KBr): 3517, 2959, 1714 cm$^{-1}$; 1H NMR (CDCl$_3$) δ: 7.19 (1H, d, 1.5 Hz, SCH), 6.93 (2H, m, thiophene CH=CH), 6.80 (1H, d, 15.5 Hz, CH=CH), 6.12 (1H, d, 15.5 Hz, CH=CH), 5.54 (1H, t, 7.0 Hz, =CHCH$_2$O), 4.81 (2H, d, 7.0 Hz, CH$_2$O), 3.82 (2H, s, COCH$_2$), 2.46 (1H, d, 15.0 Hz, H-3'), 2.30 (2H, m, H-5' & H-6') 2.13 (2H, m, H-5' & H-3'), 1.90 (3H, s, CH$_3$), 1.02 (3H, s, CH$_3$), 0.90 (3H, s, CH$_3$), 0.85 (3H, d, 6.5 Hz, CH$_3$); $^{13}$C NMR (C$_6$D$_6$) δ: 209.3, 170.4, 136.7, 135.6, 135.0, 129.9, 128.2, 126.8, 125.1, 123.1, 78.1, 61.0, 52.9, 47.1, 41.6, 37.4, 35.4, 25.2, 22.8, 20.9, 15.9; HRMS EI$^+$ m/z calc. for C$_{21}$H$_{28}$O$_4$S: 376.1708. found: 376.1720.

References: The contents of the entirety of each of which are incorporated by this reference.

1. Zeevaart, J. A.; Creelman, R. A. *Ann. Rev. Plant Physiol. Plant Mol. Biol.* 1988, 39, 439
2. McCarty, D. R. *Ann. Rev. Plant Physiol. Plant Mol. Biol.* 1995, 46, 71
3. Nambara, E.; Marion-Poll, A. *Ann. Rev. Plant Biol.* 2005, 56, 165.
4. Milborrow, B. V. *J. Exp. Bot.* 2001, 52, 1145.
5. Kushiro, T.; Okamoto, M.; Nakabayashi, K.; Yamagishi, K.; Kitamura, S.; Asami, T.; Hirai, N.; Koshiba, T.; Kamiya, Y.; Nambara, E. *The EMBO Journal* 2004, 23, 1647.
6. Schwartz, S. H.; Tan, B. C.; Gage, D. A.; Zeevaart, J. A. D.; McCarty, D. R. *Science* 1997, 276, 1872.
7. Iuchi, S.; Kobayashi, M.; Taji, T.; Naramoto, M.; Seki, M.; Kato, T.; Tabata, S.; Kakubari, Y.; Yamaguchi-Shinozaki, K.; Shinozaki, K. *The Plant Journal* 2001, 27, 325.
8. Qin, X.; Zeevaart, J. A. D. *PNAS* 1999, 96, 15354.
9. Burbidge, A.; Grieve, T. M.; Jackson, A.; Thompson, a.; McCarty, D. R.; Taylor, I. B. *The Plant Journal* 1999, 17, 427.
10. Chernys, J. T.; Zeevaart, J. A. D. *Plant Physiol.* 2000, 124, 343.

11. Iuchi, S.; Kobayashi, M.; Yamaguchi-Shinozaki, K.; Shinozaki, K. *Plant Physiol.* 2000, 123, 553.
12. Tan, B.-C.; Joseph, L. M.; Deng, W.-T.; Liu, L.; Li, Q.-B.; Cline, K.; McCarty, D. R. *The Plant Journal* 2003, 35, 44.
13. Endo, A.; Sawada, Y.; Takahashi, H.; Okamoto, M.; Ikegami, K.; Koiwai, H.; Seo, M.; Toyomasu, T.; Mitsuhashi, W.; Shinozaki, K.; Nakazono, M.; Kamiya, Y.; Koshiba, T.; Nambara, E. *Plant Physiol.* 2008, pp. 108.116632.
14. Nagamune, K.; Hicks, L. M.; Fux, B.; Brossier, F.; Chini, E. N.; Sibley, L. D. *Nature* 2008, 451, 207.
15. Toh, S.; Imamura, A.; Watanabe, A.; Nakabayashi, K.; Okamoto, M.; Jikumaru, Y.; Hanada, A.; Aso, Y.; Ishiyama, K.; Tamura, N.; Iuchi, S.; Kobayashi, M.; Yamaguchi, S.; Kamiya, Y.; Nambara, E.; Kawakami, N. *Plant Physiol.* 2008, 146, 1368.
16. Creelman, R. A.; Bell, E.; Mullet, J. E. *Plant Physiol.* 1992, 99, 1258.
17. Kitahata, N.; Han, S.-Y.; Noji, N.; Saito, T.; Kobayashi, M.; Nakano, T.; Kuchitsu, K.; Shinozaki, K.; Yoshida, S.; Matsumoto, S. *Bioorganic & Medicinal Chemistry* 2006, 14, 5555.
18. Han, S.-Y.; Kitahata, N.; Sekimata, K.; Saito, T.; Kobayashi, M.; Nakashima, K.; Yamaguchi-Shinozaki, K.; Shinozaki, K.; Yoshida, S.; Asami, T. *Plant Physiol.* 2004, 135, 1574.
19. Baumeler, A.; Brade, W.; Haag, A.; Eugster, C. H. *Helv. Chim. Acta* 1990, 73, 700.
20. Lamb, N.; Abrams, S. R. *Canadian Journal of Chemistry* 1990, 68, 1151.
21. Isler, O.; Lindlar, H.; Montavon, M.; Rüegg, R.; Saucy, G.; Zeller, P. *Helv. Chim. Acta* 1956, 39, 2041.
22. Nakagawa, I.; Hata, T. *Tetrahedron Letters* 1975, 17, 1409.
23. Furuichi, N.; Hara, H.; Osaki, T.; Mori, H.; Katsumura, S. *Angew. Chem., Int. Ed.* 2002, 41, 1023.
24. Schwartz, S. H.; Tan, B. C.; McCarty, D. R.; Welch, W.; Zeevaart, J. A. D. *Biochimica et Biophysica Acta (BBA)—General Subjects* 2003, 1619, 9.
25. Kloer, D. P.; Ruch, S.; Al-Babili, S.; Beyer, P.; Schulz, G. E. *Science* 2005, 308, 267.
26. Schwede, T.; Kopp, J.; Guex, N.; Peitsch, M. C. *Nucl. Acids Res.* 2003, 31, 3381.
27. Creelman, R. A.; Zeevaart, J. A. D. *Plant Physiol.* 1985, 77, 25.
28. Huang, D.; Wu, W.; Abrams, S. R.; Cutler, A. J. *Journal of Experimental Botany* 2008, 59, 2991.
29. Cutler, A. J.; Rose, P. A.; Squires, T. M.; Loewen, M. K.; Shaw, A. C.; Quail, J. W.; Krochko, J. E.; Abrams, S. R. *Biochemistry* 2000, 39, 13614.
30. Yamaguchi-Shinozaki, K.; Shinozaki, K. *Plant Physiol.* 1993, 101, 1119.
31. Norris, S. R.; Meyer, S. E.; Callis, J. *Plant Molecular Biology* 1993, 21, 895.
32. Han, S.-y.; Inoue, H.; Terada, T.; Kamoda, S.; Saburi, Y.; Sekimata, K.; Saito, T.; Kobayashi, M.; Shinozaki, K.; Yoshida, S.; Asami, T. *Bioorganic & Medicinal Chemistry Letters* 2002, 12, 1139.
33. Abe, M.; Matsuki, H.; Domae, M.; Kuwata, H.; Kudo, I.; Nakanishi, Y.; Hara, N.; Mitsuyama, T.; Furukawa, T. *Am. J. Respir. Cell Mol. Biol.* 1996, 15, 565.
34. Wilen, R. W.; Hays, D. B.; Mandel, R. M.; Abrams, S. R.; Moloney, M. M. *Plant Physiol* 1993, 101, 469.
35. Guo, S.; Boyd, J.; Sammynaiken, R.; Loewen, M. C. *Biochemistry and Cell Biology* 2008, In Press.
36. Bradford, M. M. *Analytical Biochemistry* 1976, 72, 248.
37. Nicolas Guex, M. C. P. *Electrophoresis* 1997, 18, 2714.
38. Morris, G. M.; Goodsell, D. S.; Halliday, R. S.; Huey, R.; Hart, W. E.; Belew, R. K.; Olson, A. J. *Journal of Computational Chemistry* 1998, 19, 1639.
39. Owen, S. J.; Abrams, S. R. In *Plant Hormones: Methods and Protocols, Second Edition*; Cutler, S., Bonetta, D., Eds.; Humana Press, a part of Springer Science+Business Media, 2008; Vol. 495, in press.
40. Walker-Simmons, M. K. Plant, *Cell and Environment* 1988, 11, 769.
41. Livak, K. J.; Schmittgen, T. D. *Methods* 2001, 25, 402.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A compound of formula (I):

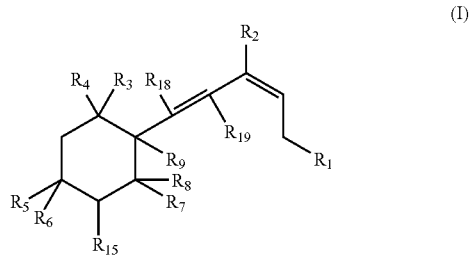

wherein:
$R_1$ is —$SR_{10}$, —O—C(O)—$R_{11}$, —$NR_{12}R_{13}$, where $R_{10}$ is a $C_{1-8}$-alkyl group or a phenyl group unsubstituted or substituted by a $C_{1-4}$-alkyl group, $R_{11}$ is a thiophenenyl, furanyl or pyrrolyl group, $R_{12}$ is H or a $C_{1-4}$-alkyl group and $R_{13}$ is a $C_{1-8}$-alkyl group or a phenyl group unsubstituted or substituted by a $C_{1-4}$-alkyl group;
$R_2$ is H or a $C_{1-4}$-alkyl group;
$R_3$ and $R_4$ are independently H or $C_{1-4}$-alkyl groups;
$R_5$ and $R_6$ are independently H, OH or $OR_{14}$, or taken together are =O, where $R_{14}$ is a protecting group;
$R_7$ is H or a $C_{1-4}$-alkyl group; and,
$R_8$ is H, $R_9$ is OH and $R_{15}$ is H, or $R_{15}$ is H and $R_8$ and $R_9$ taken together are —O—, or $R_9$ is OH and $R_8$ and $R_{15}$ taken together form a bond; and,
$R_{18}$ and $R_{19}$ are both H, or $R_{18}$ and $R_{19}$ taken together form a bond, or a plant physiologically acceptable salt thereof.

2. The compound according to claim 1, wherein $R_1$ is —$SR_{10}$ and $R_{10}$ is ethyl or phenyl.

3. The compound according to claim 1, wherein $R_1$ is —O—C(O)—$R_{11}$ and $R_{11}$ is thiophenenyl.

4. The compound according to claim 1, wherein $R_1$ is —$NR_{12}R_{13}$ and $R_{12}$ is H and $R_{13}$ is phenyl.

5. The compound according to claim 1, wherein $R_2$ is methyl, $R_3$ is methyl, $R_4$ is methyl, one of $R_5$ and $R_6$ is OH or $R_5$ and $R_6$ taken together are =O, $R_7$ is methyl, $R_{15}$ is H, and $R_{18}$ and $R_{19}$ taken together form a bond.

6. The compound according to claim 2, wherein $R_2$ is methyl, $R_3$ is methyl, $R_4$ is methyl, one of $R_5$ and $R_6$ is OH or O-(tert-butyldimethylsilyl) or $R_5$ and $R_6$ taken together are =O, $R_7$ is methyl, $R_{15}$ is H, and $R_{18}$ and $R_{19}$ taken together form a bond.

7. (4S,5R)-(3'Z)-4-(5'-(Ethylthio)-3'-methylpent-3'-en-1'-ynyl)-4-hydroxy-3,3,5-trimethylcyclohexanone, (4R,5S)-(3'Z)-4-(5'-(ethylthio)-3'-methylpent-3'-en-1'-ynyl)-4-hydroxy-3,3,5-trimethylcyclohexanone,
(4S,5R/4R,5S)-(3'Z)-4-(5'-(ethylthio)-3'-methylpent-3'-en-1'-ynyl)-4-hydroxy-3,3,5-trimethylcyclohexanone,
(1S,4R,6R)-(3'Z)-1-(5'-(ethylthio)-3'-methylpent-3'-en-1'-ynyl)-2,2,6-trimethylcyclohexane-1,4-diol,
(1R,4R,6R)-(3'Z)-1-(5'-(ethylthio)-3'-methylpent-3'-en-1'-ynyl)-2,2,6-trimethylcyclohexane-1,4-diol,
(2Z,4E)-5-(1-hydroxy-2',2',6'-trimethyl-4'-oxocyclohexyl)-3-methylpenta-2,4-dienyl 2-(thiophen-2''-yl) acetate,
(1R,3S,6R)-(3'Z)-1,5,5-trimethyl-6-(3'-methyl-5'-(phenylthio)-pent-3'-en-1'-ynyl)-7-oxa-bicyclo[4.1.0]heptan-3-ol,
(1R,3S,6R)-(3'Z)-1,5,5-trimethyl-6-(3'-methyl-5'-(phenylamino)-pent-3'-en-1'-ynyl)-7-oxabicyclo[4.1.0]heptan-3-ol, or a plant physiologically acceptable salt thereof.

8. A method of inhibiting 9-cis-epoxycarotenoid dioxygenase (NCED) in a plant or seed comprising administering to the plant or seed a 9-cis-epoxycarotenoid dioxygenase inhibiting effective amount of a compound of formula (I):

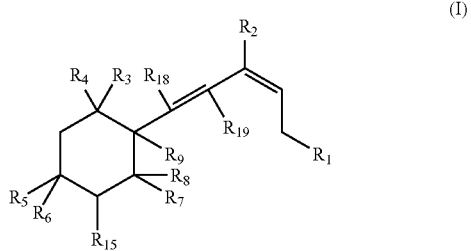

(I)

wherein:
$R_1$ is —$SR_{10}$, —O—C(O)—$R_{11}$, —$NR_{12}R_{13}$, where $R_{10}$ is a $C_{1-8}$-alkyl group or a phenyl group unsubstituted or substituted by a $C_{1-4}$-alkyl group, $R_{11}$ is a thiophenenyl, furanyl or pyrrolyl group, $R_{12}$ is H or a $C_{1-4}$-alkyl group and $R_{13}$ is a $C_{1-8}$-alkyl group or a phenyl group unsubstituted or substituted by a $C_{1-4}$-alkyl group;
$R_2$ is H or a $C_{1-4}$-alkyl group;
$R_3$ and $R_4$ are independently H or $C_{1-4}$-alkyl groups;
$R_5$ and $R_6$ are independently H, OH or $OR_{14}$, or taken together are =O, where $R_{14}$ is a protecting group;
$R_7$ is H or a $C_{1-4}$-alkyl group; and, $R_8$ is H, $R_9$ is OH and $R_{15}$ is H, or $R_{15}$ is H and $R_8$ and $R_9$ taken together are —O—, or $R_9$ is OH and $R_8$ and $R_{15}$ taken together form a bond; and,
$R_{18}$ and $R_{19}$ are both H, or $R_{18}$ and $R_{19}$ taken together form a bond, or a plant physiologically acceptable salt thereof.

9. The method according to claim 8, wherein $R_1$ is —$SR_{10}$ and $R_{10}$ is ethyl or phenyl, or $R_1$ is —O—C(O)—$R_{11}$ and $R_{11}$ is thiophenenyl, or $R_1$ is —$NR_{12}R_{13}$ and $R_{12}$ is H and $R_{13}$ is phenyl.

10. The method according to claim 8, wherein $R_2$ is methyl, $R_3$ is methyl, $R_4$ is methyl, one of $R_5$ and $R_6$ is OH or $R_5$ and $R_6$ taken together are =O, $R_7$ is methyl, $R_{15}$ is H, and $R_{18}$ and $R_{19}$ taken together form a bond.

11. The method according to claim 9, wherein $R_2$ is methyl, $R_3$ is methyl, $R_4$ is methyl, one of $R_5$ and $R_6$ is OH or $R_5$ and $R_6$ taken together are =O, $R_7$ is methyl, $R_{15}$ is H, and $R_{18}$ and $R_{19}$ taken together form a bond.

12. The method according to claim 8, wherein the compound is (4S,5R)-(3'Z)-4-(5'-(ethylthio)-3'-methylpent-3'-en-1'-ynyl)-4-hydroxy-3,3,5-trimethylcyclohexanone, (4R,5S)-(3'Z)-4-(5'-(ethylthio)-3'-methylpent-3'-en-1'-ynyl)-4-hydroxy-3,3,5-trimethylcyclohexanone, (4S,5R4R,5S)-(3'Z)-4-(5-(ethylthio)-3'-methylpent-3'-en-1'-ynyl)-4-hydroxy-3,3,5-trimethylcyclohexanone, (1S,4R,6R)-(3'Z)-1-(5'-(ethylthio)-3'-methylpent-3'-en-1'-ynyl)-2,2,6-trimethylcyclohexane-1,4-diol, (1R,4R,6R)-(3'Z)-1-(5'-(ethylthio)-3'-methylpent-3'-en-1'-ynyl)-2,2,6-trimethylcyclohexane-1,4-diol, (2Z,4E)-5-(1'-hydroxy-2',2',6'-trimethyl-4'-oxocyclohexyl)-3-methylpenta-2,4-dienyl 2-(thiophen-2''-yl) acetate, (1R,3S,6R)-(3'Z)-1,5,5-trimethyl-6-(3'-methyl-5'-(phenylthio)-pent-3'-en-1'-ynyl)-7-oxa-bicyclo[4.1.0]heptan-3-ol, (1R,3S,6R)-(3'Z)-1,5,5-trimethyl-6-(3'-methyl-5'-(phenylamino)-pent-3'-en-1'-ynyl)-7-oxabicyclo[4.1.0]heptan-3-ol, or a plant physiologically acceptable salt thereof.

13. The method according to claim 8, further comprising determining that regulation of seed maturation, desiccation tolerance, dormancy or adaptation to environmental stress has occurred in the plant or seed.

14. The method according to claim 12, further comprising determining that regulation of seed maturation, desiccation tolerance, dormancy or adaptation to environmental stress has occurred in the plant or seed.

* * * * *